United States Patent
Deason et al.

(10) Patent No.: US 6,605,721 B2
(45) Date of Patent: Aug. 12, 2003

(54) INTERMEDIATES FOR MAKING HIV-PROTEASE INHIBITORS AND METHODS FOR MAKING HIV-PROTEASE INHIBITORS

(75) Inventors: Michael E. Deason, Poway, CA (US); Kathleen R. Whitten, San Diego, CA (US)

(73) Assignees: Agouron Pharmaceuticals, Inc., San Diego, CA (US); Japan Tobacco, Inc., Tokyo (JP)

( * ) Notice: Subject to any disclaimer, the term of this patent is extended or adjusted under 35 U.S.C. 154(b) by 0 days.

(21) Appl. No.: 10/278,442

(22) Filed: Oct. 22, 2002

(65) Prior Publication Data

US 2003/0135051 A1 Jul. 17, 2003

Related U.S. Application Data

(62) Division of application No. 10/112,721, filed on Apr. 2, 2002, now Pat. No. 6,512,135, which is a division of application No. 09/888,593, filed on Jun. 26, 2001, now Pat. No. 6,407,285, which is a division of application No. 09/300,835, filed on Apr. 28, 1999, now Pat. No. 6,303,786, which is a division of application No. 08/923,943, filed on Sep. 5, 1997, now Pat. No. 5,962,725.

(60) Provisional application No. 60/025,515, filed on Sep. 5, 1996, and provisional application No. 60/025,517, filed on Sep. 5, 1996.

(51) Int. Cl.[7] ........................................... C07D 217/12

(52) U.S. Cl. ....................................... 546/146

(58) Field of Search ........................................ 546/146

(56) References Cited

U.S. PATENT DOCUMENTS

| | | | |
|---|---|---|---|
| 5,063,208 A | 11/1991 | Rosenberg et al. | 514/19 |
| 5,142,056 A | 8/1992 | Kempe et al. | 546/265 |
| 5,157,041 A | 10/1992 | Handa et al. | 514/314 |
| 5,196,438 A | 3/1993 | Martin et al. | 514/311 |
| 5,204,471 A | 4/1993 | Negele et al. | 546/144 |
| 5,235,039 A | 8/1993 | Heath, Jr. et al. | 530/328 |
| 5,256,783 A | 10/1993 | Gokhale et al. | 546/146 |
| 5,434,265 A | 7/1995 | Fritz et al. | 546/146 |
| 5,463,104 A | 10/1995 | Vasquez et al. | 546/89 |
| 5,475,136 A | 12/1995 | Fritz et al. | 564/162 |
| 5,484,926 A | 1/1996 | Dressman et al. | 546/114 |
| 5,491,166 A | 2/1996 | Kaldor et al. | 514/481 |
| 5,502,061 A | 3/1996 | Hui et al. | 514/311 |
| 5,508,407 A | 4/1996 | Kaldor et al. | 546/169 |
| 5,514,802 A | 5/1996 | Fritz et al. | 546/146 |
| 5,527,829 A | 6/1996 | Kalish | 514/604 |
| 5,554,653 A | 9/1996 | Hui et al. | 514/605 |
| 5,705,647 A | 1/1998 | Babu et al. | 546/146 |
| 5,846,993 A | 12/1998 | Dressman et al. | 514/423 |
| 5,905,077 A | 5/1999 | Jungheim et al. | 514/222.2 |
| 5,925,759 A | 7/1999 | Babu et al. | 546/164 |
| 5,962,725 A | 10/1999 | Deason et al. | 560/130 |
| 6,084,107 A | 7/2000 | Babu et al. | 548/485 |

FOREIGN PATENT DOCUMENTS

| | | |
|---|---|---|
| CA | 2075666 A1 | 2/1993 |
| EP | 0337714 A2 | 10/1989 |
| EP | 0346847 A2 | 12/1989 |
| EP | 0356223 A2 | 2/1990 |
| EP | 0361341 A2 | 4/1990 |
| EP | 0402646 A1 | 12/1990 |
| EP | 0432694 A2 | 6/1991 |
| EP | 0432695 A2 | 6/1991 |
| EP | 0434365 A2 | 6/1991 |
| EP | 0490667 A2 | 6/1992 |
| EP | 0498680 A1 | 8/1992 |
| EP | 0526009 A1 | 2/1993 |
| EP | 0533000 A1 | 3/1993 |
| EP | 0539192 A1 | 4/1993 |
| EP | 0560268 A1 | 9/1993 |
| EP | 579223 | 1/1994 |
| WO | 91/08221 | 6/1991 |
| WO | 93/04043 | 3/1993 |
| WO | 93/13066 | 7/1993 |
| WO | 93/23379 | 11/1993 |
| WO | 94/04492 | 3/1994 |
| WO | 94/05639 | 3/1994 |
| WO | 95/09843 | 4/1995 |
| WO | 96/28423 | 9/1996 |
| WO | 97/11937 | 4/1997 |
| WO | 97/11938 | 4/1997 |
| WO | 97/30993 | 8/1997 |

OTHER PUBLICATIONS

Alley et al., "Feasibility of Drug Screening with Panels of Human Tumor Cell Lines Using a Microculture Tetrazolium Assay", *Cancer Research* 48:589–601 (Feb. 1, 1988).
Celis et al., "Chain–terminating Mutants Affecting a Periplasmic Binding Protein Involved in the Active Transport of Arginine and Ornithine in *Escherichia coli*", *Journal of Biological Chemistry* 256(2):773–779 (1981).
Chong, et al., *J. Med. Chem.* 36:2575–2577 (1993).
Gao et al., "Vicinal Diol Cyclic Sulfates: Like Epoxides Only More Reactive", *J. Am. Chem. Soc.* 110:7538–7539 (1988).
Ghosh et al., *J. Med. Chem.* 36(16):2300–2310 (1993).
Ghosh et al., *J. Med. Chem.* 36(7):924–927 (1993).
Ghosh et al., *J. Med. Chem.* 63(2):292–294 (1993).
Gilbert et al., *J. Chem. Soc. Perkin Trans.* 2:475–479 (1992).
Houpis, et al., *Tetrahedron Letters* 34(16):2593–2596 (1993).
Lyle et al., *J. Med. Chem.* 34(3):1228–1230 (1991).
Mash et al., "1,4–Di–o–alkyl Threitols from Tartaric Acid", *Org. Synthesis, Coll.* 8:155–161.

(List continued on next page.)

*Primary Examiner*—Zinna Northington Davis
(74) *Attorney, Agent, or Firm*—Fitzpatrick, Cella, Harper & Scinto

(57) ABSTRACT

HIV protease inhibitors inhibit or block the biological activity of the HIV protease enzyme, causing the replication of the HIV virus to terminate. These compounds can be prepared by the novel methods of the present invention using the novel inventive compounds and intermediates.

19 Claims, No Drawings

OTHER PUBLICATIONS

Menge et al., "Structure–Function Analysis of the Mammalian DNA Polymerase Active Site: role of Aspartic Acid 256, Arginine 254, and Arginine 258 in Nucleotidyl Transfer", *Biochemistry* 34:19934–19942 (1995).

Morrison, "Kinetics of the Reversible Inhibition of EnzymeoCatalysed Reactions by Tight–Binding Inhibitors", *Biochim. Biophys. Acta* 185:269–286 (1969).

Mukharji et al., *Indian J. Chem*.EN. 515–523, (1971) as abstracted in DATABASE XFIRE<Beilstein, 3–methoxy–2–methyl–benzoic acid ethyl ester.

Ozturk et al., "Synthesis of a Chiral Monosubstituted Derivative of Bis(ethylenedithio)tetrathiafulvalene: Reaction of the cyclic Sulfate Ester of R,R–1,4–Difluorobutane–2,3–idiol with 2–Thioxo–1,3–dithiole–4,5–dithiolate", *J. Mater. Chem.* 5(10):1553–1556 (1995).

Peltier et al., "Contribution a l'etude du groupe carboxylique. Absorption infrarouge et ionization", *Bulletin de la Societe chimique de France* 1141–1147 (1960).

Prasad, et al., *Chemistry and Biology, Proceedings of the Twelfth American Peptide Symposium* 721–722 (1991).

Ratner et al., "Complete nucleotide sequence of the AIDS virus, HTLV–III", *Nature* (Jan. 24, 1985) vol. 313.

Rich et al., *Chem. Abstracts* 114:15 (Abstract 143998g) (1991).

Rich et al., *J. Med. Chem.* 34(3):1222–1225 (1991).

Roberts et al., *Science* 248:358–361 (1990).

Rose et al., "Regulation of Autoproteolysis of the HIV–1 and HIV–2 Proteases with Engineered Amino Acid Substitutions", *Journal of Biological Chemistry* 268(16): 11939–11945 (1993).

Takano et al., Selective Manipulation of Hydroxy Groups in (2S, #S)–Threitol, *Synthesis* 811–817 (Oct. 1986).

Thaisrivongs et al., *J. Med. Chem.* 34(8):2344–2356 (1991).

Thompson et al., *J. Am. Chem. Soc.*115(2):801–802 (1993).

Townsend et al., "Novel Copper Complexes of chiral Diphosphines: Preparation, Structure, and Use to Form Rhodium Complex Catalysts for Chiral Hydrogenations", *J. Org. Chem.* 45:2995–2999 (1980).

Vanhessche et al., "Catalytic Asymmetric Synthesis of Ne Halogenated Chiral Synthons", *Chem. Eur. J.* 3(4) (1997).

Young et al., *J. Med. Chem.* 35(10):1702–1709 (1992).

INTERMEDIATES FOR MAKING HIV-PROTEASE INHIBITORS AND METHODS FOR MAKING HIV-PROTEASE INHIBITORS

RELATED APPLICATION DATA

This application is a division of U.S. patent application Ser. No. 10/112,721 filed Apr. 2, 2002, now U.S. Pat. No. 6,512,135 which is a division of U.S. patent application Ser. No. 09/888,593 filed Jun. 26, 2001, now U.S. Pat. No. 6,407,285, which is a division of U.S. patent application Ser. No. 09/300,835 filed Apr. 28, 1999, now U.S. Pat. No. 6,303,786, issued Oct. 16, 2001, which is a division of U.S. patent application Ser. No. 08/923,943, filed Sep. 5, 1997, now U.S. Pat. No. 5,962,725, issued Oct. 5, 1999, which claims benefit of priority under 35 U.S.C. §119 to U.S. Provisional Patent Application No. 60/025,515 filed Sep. 5, 1996, the disclosures of each of which are incorporated herein by reference.

This application claims priority benefits under 35 U.S.C. § 119 based on U.S. Provisional Patent Appln. Ser. No. 60/025,517, filed Sept. 5, 1996. This provisional application is entirely incorporated herein by reference. Additionally, this application relates to the following U.S. patent applications:

| U.S. Patent Appln. No. | Filing Date |
| --- | --- |
| 08/133,543 | Oct. 7, 1993 |
| 08/133,696 | Oct. 7, 1993 |
| 08/190,764 | Feb. 2, 1994 |
| 08/481,833 | Jun. 7, 1995 |
| 08/708,411 | Sep. 5, 1996 |

Each of these U.S. patent applications also is entirely incorporated herein by reference.

INTRODUCTION

Treatment of HIV-infected individuals is one of the most pressing biomedical problems of recent times. A promising new therapy has emerged as an important method for preventing or inhibiting the rapid proliferation of the virus in human tissue. HIV-protease inhibitors block a key enzymatic pathway in the virus resulting in substantially decreased viral loads, which slows the steady decay of the immune system and its resulting deleterious effects on human health. The HIV-protease inhibitor nelfinavir mesylate of formula 7

Formula 7

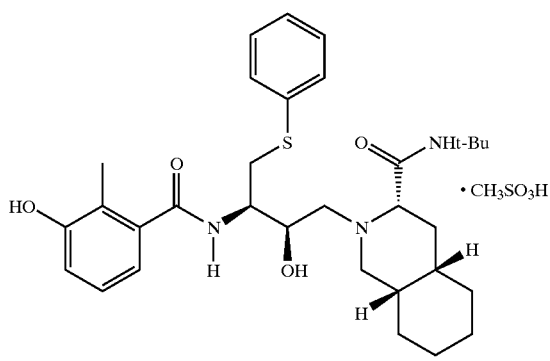

has been shown to be an effective treatment for HIV-infected individuals. Nelfinavir mesylate is disclosed in U.S. Pat. No. 5,484,926, issued Jan. 16, 1996. This patent is entirely incorporated by reference into this patent application.

The present inventors have discovered useful intermediate compounds that can be used in several reaction schemes to make nelfinavir mesylate. The present inventors also have discovered new methods for making nelfinavir mesylate from the free base nelfinavir of formula 4:

Formula 4

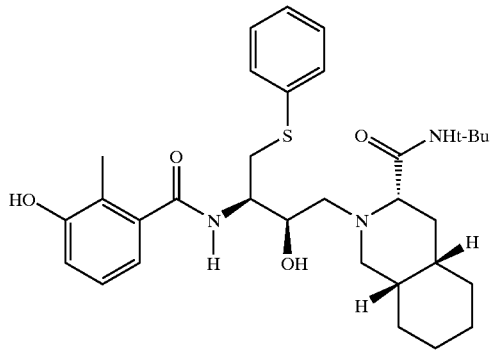

The nelfinavir free base also is disclosed in U.S. Pat. No. 5,484,926.

SUMMARY OF THE INVENTION

It is an object of this invention to provide compounds and intermediates useful for making HIV-protease inhibitors and methods of making HIV-protease inhibitors. Such inhibitors are useful for treating HIV-infected individuals.

In a first aspect, the invention relates to compounds of formula 3:

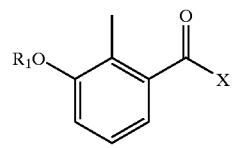

wherein $R_1$ is alkyl; cycloalkyl; heterocycloalkyl; aryl; heteroaryl; or a group of formula 8

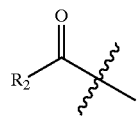

wherein $R_2$ is an alkyl group, a cycloalkyl group, a heterocycloalkyl group, or O—$R_6$,
wherein $R_6$ is an alkyl group, an aralkyl group, or an aryl group;
or further wherein $R_1$ is a group of formula 9

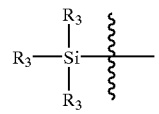

wherein each $R_3$ is independently an alkyl group, a cydoalkyl group, a heterocycloalkyl group, an aryl group, or a heteroaryl group;
or further wherein $R_1$ is a group of formula 10

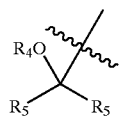

wherein $R_4$ and each $R_5$ independently are an alkyl group, a cycloalkyl group, a heterocycloalkyl group, an aryl group, or a heteroaryl group; and X is OH; $OR_7$, wherein $R_7$ is alkyl or aryl; halogen; pseudohalogen; $OSO_2R_8$, wherein $R_8$ is alkyl or aryl; heteroaryl bonded through the heteroatom; or N-hydroxyheterocyclic bonded through the oxygen, with the proviso that when $R_1$ is —$CH_3$, X cannot be —$OCH_3$ or —OH, and when $R_1$ is $CH_3C(O)$—, X cannot be —OH;

or a pharmaceutically acceptable salt or solvate thereof.

In various preferred embodiments of the invention, $R_1$ is —$C(O)CH_3$ and/or X is a halogen, preferably, Cl.

In another aspect, the invention relates to compounds of formula 2:

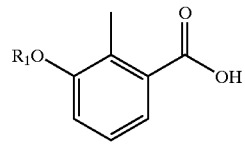

wherein $R_1$ is a $C_2$ to $C_8$ alkyl group, a cycloalkyl group, a heterocycloalkyl group, an aryl group, a heteroaryl group, or a group of formula 8

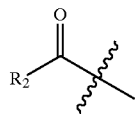

wherein $R_2$ is a $C_2$ to $C_8$ alkyl group, a cycloalkyl group, a heterocycloalkyl group, or O—$R_6$, wherein $R_6$ is an alkyl group, an aralkyl group, or an aryl group;

or further wherein $R_1$ is a group of formula 9

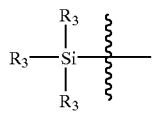

wherein each $R_3$ independently is an alkyl group, a cycloalkyl group, a heterocycloalkyl group, an aryl group, or a heteroaryl group;

or further wherein $R_1$ is a group of formula 10

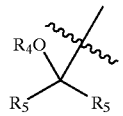

wherein $R_4$ and each $R_5$ independently are an alkyl group, a cycloalkyl group, a heterocycloalkyl group, an aryl group, or a heteroaryl group;

or a pharmaceutically acceptable salt or solvate thereof.

This invention further relates to methods for making the compounds of formulae 2 and 3. In a method for making a compound of formula 2:

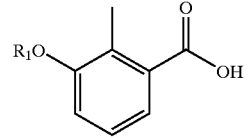

a compound according to formula 1, shown below,

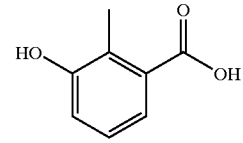

is reacted under suitable and sufficient conditions to add an $R_1$ protecting group and form a compound of formula 2. In this instance, $R_1$ is a $C_2$ to $C_8$ alkyl group; a cycloalkyl group; a heterocycloalkyl group; an aryl group; a heteroaryl group; or a group of formula 8

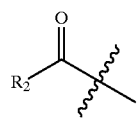

wherein $R_2$ is a $C_2$ to $C_8$ alkyl group, a cycloalkyl group, a heterocycloalkyl group, or O—$R_6$, wherein $R_6$ is an alkyl group, an aralkyl group, or an aryl group;

or $R_1$ is a group of formula 9

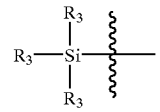

wherein each $R_3$ is independently an alkyl group, a cycloalkyl group, a heterocycloalkyl group, an aryl group, or a heteroaryl group;

or $R_1$ is a group of formula 10

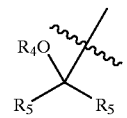

wherein $R_4$ and each $R_5$ independently are an alkyl group, a cycloalkyl group, a heterocycloalkyl group, an aryl group, or a heteroaryl group.

This invention includes a method of making a compound according to formula 3

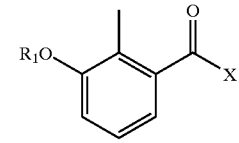

This method includes adding, under suitable and sufficient conditions, a suitable protecting group $R_1$ and a leaving group X to a compound of formula 1

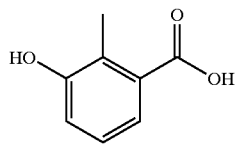

In this instance, $R_1$ is alkyl, cycloalkyl; heterocycloalkyl; aryl; heteroaryl; or a group of formula 8

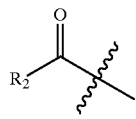

wherein $R_2$ is an alkyl group, a cycloalkyl group, a heterocycloalkyl group, or $O-R_6$, wherein $R_6$ is an alkyl group, an aralkyl group, or an aryl group;

or $R_1$ is a group of formula 9

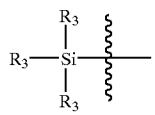

wherein each $R_3$ is independently an alkyl group, a cycloalkyl group, a heterocycloalkyl group, an aryl group, or a heteroaryl group;

or further wherein $R_1$ is a group of formula 10

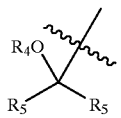

wherein $R_4$ and each $R_5$ independently are an alkyl group, a cycloalkyl group, a heterocycloalkyl group, an aryl group, or a heteroaryl group; and X is OH; $OR_7$, wherein $R_7$, is alkyl or aryl; halogen; pseudohalogen; $OSO_2R_8$, wherein $R_8$ is alkyl or aryl; heteroaryl bonded through the heteroatom; or N-hydroxyheterocyclic bonded through the oxygen, with the proviso that when $R_1$ is —$CH_3$, X cannot be —$OCH_3$ or —OH, and when $R_1$ is $CH_3C(O)$—, X cannot be —OH. As noted above, in certain embodiments, $R_1$ is —$C(O)CH_3$ and/or X is a halogen, preferably, Cl.

A compound according to formula 3, as defined above, also can be made from a compound of formula 2. The reaction proceeds by adding a suitable leaving group X to the compound of formula 2. In this instance, formula 2 is as defined below:

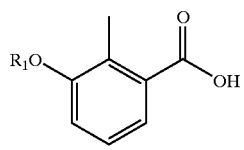

wherein $R_1$ is alkyl; cycloalkyl; heterocycloalkyl; aryl; heteroaryl; or a group of formula 8

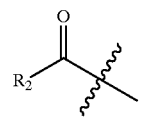

wherein $R_2$ is an alkyl group, a cycloalkyl group, a heterocycloalkyl group, or $O-R_6$, wherein $R_6$ is an alkyl group, an aralkyl group, or an aryl group;

or further wherein $R_1$ is a group of formula 9

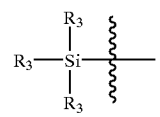

wherein each $R_3$ is independently an alkyl group, a cycloalkyl group, a heterocycloalkyl group, an aryl group, or a heteroaryl group;

or further wherein $R_1$ is a group of formula 10

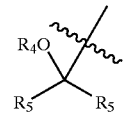

wherein $R_4$ and each $R_5$ independently are an alkyl group, a cycloalkyl group, a heterocycloalkyl group, an aryl group, or a heteroaryl group. Additionally, in this instance, X is defined as OH; $OR_7$, wherein $R_7$ is alkyl or aryl; halogen; pseudohalogen; $OSO_2R_8$, wherein $R_8$ is alkyl or aryl; heteroaryl bonded through the heteroatom; or N-hydroxyheterocyclic bonded through the oxygen. In this method, when $R_1$ is —$CH_3$, X cannot be —$OCH_3$ or —OH, and when $R_1$ is $CH_3C(O)$—, X cannot be —OH.

This invention further relates to methods for making HIV-protease inhibitors. One HIV-protease inhibitor produced by a method according to this invention is a compound of formula 4, illustrated below:

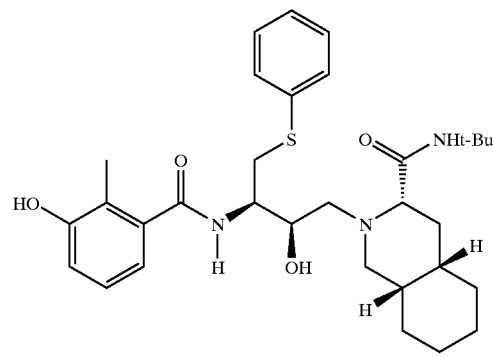

In this method, a compound of formula 3

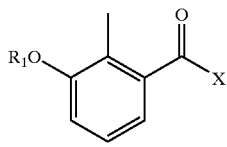

wherein $R_1$ is alkyl; cycloalkyl; heterocycloalkyl; aryl; heteroaryl; or a group of formula 8

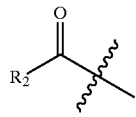

wherein $R_2$ is an alkyl group, a cycloalkyl group, a heterocycloalkyl group, or O—$R_6$, wherein $R_6$ is an alkyl group, an aralkyl group, or an aryl group;

or further wherein $R_1$ is a group of formula 9

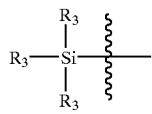

wherein each $R_3$ independently is an alkyl group, a cycloalkyl group, a heterocycloalkyl group, an aryl group, or a heteroaryl group;

or further wherein $R_1$ is a group of formula 10

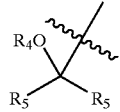

wherein $R_4$ and each $R_5$ independently are an alkyl group, a cycloalkyl group, a heterocycloalkyl group, an aryl group, or a heteroaryl group; and X is OH; $OR_7$, wherein $R_7$ is alkyl or aryl; halogen; pseudohalogen; $OSO_2R_8$, wherein $R_8$ is alkyl or aryl; heteroaryl bonded through the heteroatom; or N-hydroxyheterocyclic bonded through the oxygen, is reacted under suitable and sufficient conditions to form the compound of formula 4. Again, for one preferred embodiment of this process, the variable $R_1$ represents —$C(O)CH_3$ and/or the variable X represents Cl.

The compound according to formula 4, identified above, also can be prepared by deprotecting a compound of formula 5

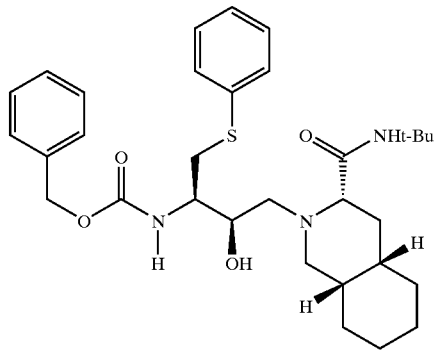

and reacting with it, under sufficient conditions, a compound of formula 3. In this instance, the compound according to formula 3 is

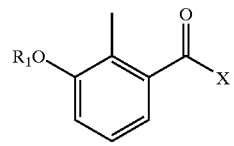

wherein $R_1$ is alkyl; cycloalkyl; heterocycloalkyl; aryl; heteroaryl; or a group of formula 8

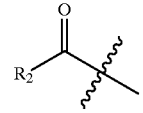

wherein $R_2$ is an alkyl group, a cycloalkyl group, a heterocycloalkyl group, or O—$R_6$, wherein $R_6$ is an alkyl group, an aralkyl group, or an aryl group;
or further wherein $R_1$ is a group of formula 9

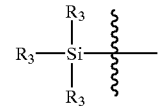

wherein each $R_3$ independently is an alkyl group, a cydoalkyl group, a heterocydoalkyl group, an aryl group, or a heteroaryl group;
or further wherein $R_1$ is a group of formula 10

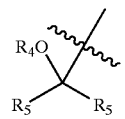

wherein $R_4$ and each $R_5$ independently are an alkyl group, a cycloalkyl group, a heterocycloalkyl group, an aryl group, or a heteroaryl group; and
X is OH; $OR_7$, wherein $R_7$ is alkyl or aryl; halogen; pseudohalogen;. $OSO_2R_8$, wherein $R_1$ is alkyl or aryl; heteroaryl bonded through the heteroatom; or N-hydroxyheterocyclic bonded through the oxygen.

In another embodiment of this invention, a compound of formula 4, as identified above, can be prepared by combining a compound of formula 3:

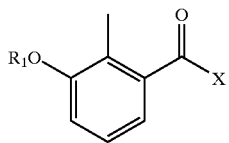

wherein $R_1$ is alkyl; cycloalkyl; heterocycloalkyl; aryl; heteroaryl; or a group of formula 8

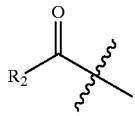

wherein $R_2$ is an alkyl group, a cycloalkyl group, a heterocycloalkyl group, or O—$R_6$, wherein $R_6$ is an alkyl group, an aralkyl group, or an aryl group;

or further wherein $R_1$ is a group of formula 9

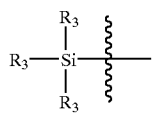

wherein each $R_3$ independently is an alkyl group, a cycloalkyl group, a heterocycloalkyl group, an aryl group, or a heteroaryl group;

or further wherein $R_1$ is a group of formula 10

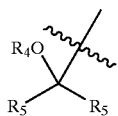

wherein $R_4$ and each $R_5$ independently are an alkyl group, a cycloalkyl group, a heterocycloalkyl group, an aryl group, or a heteroaryl group; and X is OH; $OR_7$, wherein $R_7$ is alkyl or aryl; halogen; pseudohalogen; $OSO_2R_8$, wherein $R_8$ is alkyl or aryl; heteroaryl bonded through the heteroatom; or N-hydroxyheterocyclic bonded through the oxygen, with a compound of formula 6

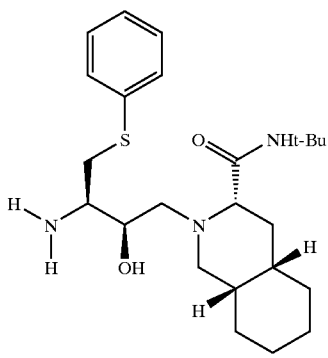

under conditions sufficient and suitable to obtain the compound of formula 4.

This invention further relates to methods of making a compound of formula 7. In one embodiment, the compound of formula 7

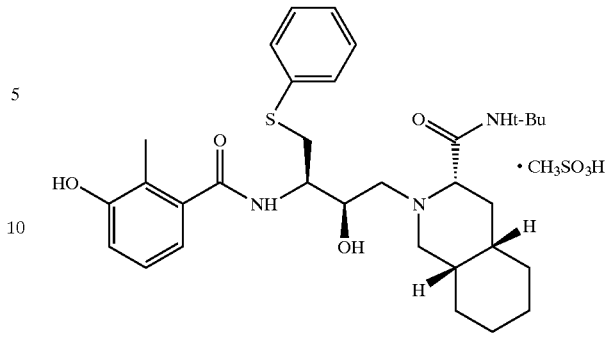

is produced by converting a compound of formula 4

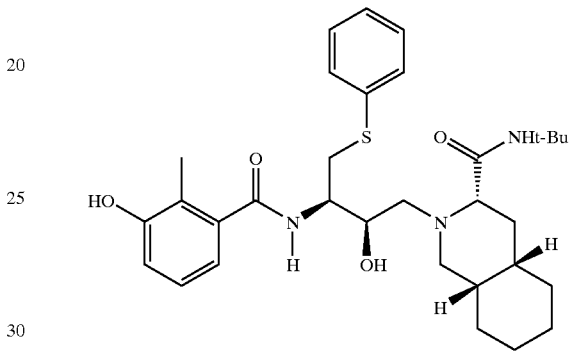

under sufficient and suitable conditions to the compound of formula 7. In this method, the conversion of the compound of formula 4 to the compound of formula 7 takes place by:

(a) contacting the compound of formula 4 with an organic solvent;

(b) contacting the compound of formula 4 with methanesulfonic acid under conditions sufficient to form a compound of formula 7; and (c) spray drying the compound of formula 7. In a more specific embodiment of this method, the organic solvent is ethanol.

In another method for making a compound of formula 7 from a compound of formula 4, the following procedure is followed:

(a) the compound of formula 4, a suitable solvent, and methanesulfonic acid are combined to form the compound of formula 7, the compound of formula 7 being dissolved in solution;

(b) a first antisolvent is added to the solution containing the compound of formula 7;

(c) the compound of formula 7 and the first antisolvent are agitated together to form a product having a solid phase and a liquid phase; and (d) the product is filtered and washed with a second antisolvent, the second antisolvent being the same as or different from the first antisolvent, to obtain a solid final product according to formula 7. After the solid final product is washed, it can be dred by any appropriate method or means. Tetrahydrofuran can be used as the solvent, and diethylether can be used as at least one antisolvent, preferably at least the first antisolvent.

This invention also relates to a method of making a compound according to formula 4 (as defined above) from a compound according to formula 2. In this method, a compound according to formula 2 is reacted under sufficient and suitable conditions to form the compound of formula 4. In this instance, the compound of formula 2 is defined as follows:

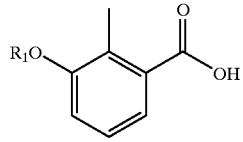

wherein $R_1$ is alkyl; cycloalkyl; heterocycloalkyl; aryl; heteroaryl; a group of formula 8

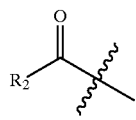

wherein $R_2$ is an alkyl group, a cycloalkyl group, a heterocycloalkyl group, or O—$R_6$, wherein $R_6$ is an alkyl group, an aralkyl group, or an aryl group;

or further wherein $R_1$ is a group of formula 9

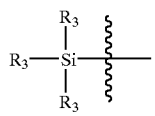

wherein each $R_3$ independently is an alkyl group, a cycloalkyl group, a heterocycloalkyl group, an aryl group, or a heteroaryl group;

or further wherein $R_1$ is a group of formula 10

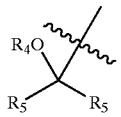

wherein $R_4$ and each $R_5$ independently are an alkyl group, a cycloalkyl group, a heterocycloalkyl group, an aryl group, or a heteroaryl group.

Yet another embodiment of this invention relates to a method of making a compound of formula 7, defined above. In this method, a compound according to formula 5

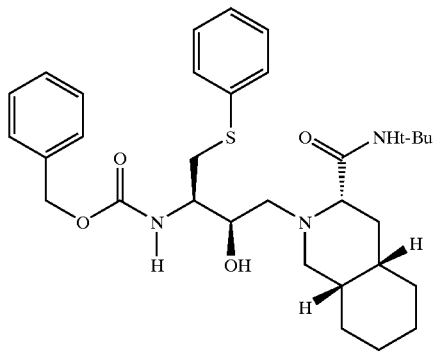

is deprotected. Then, the deprotected compound of formula 5 is reacted, under sufficient and suitable conditions, with a compound of formula 3. Formula 3, in this instance, is defined as follows:

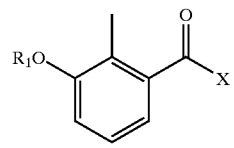

wherein $R_1$ is alkyl; cycloalkyl; heterocycloalkyl; aryl; heteroaryl; or a group of formula 8

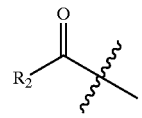

wherein $R_2$ is an alkyl group, a cycloalkyl group, a heterocycloalkyl group, or O—$R_6$, wherein $R_6$ is an alkyl group, an aralkyl group, or an aryl group;

or further wherein $R_1$ is a group of formula 9

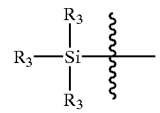

wherein each $R_3$ independently is an alkyl group, a cycloalkyl group, a heterocycloalkyl group, an aryl group, or a heteroaryl group;

or further wherein $R_1$ is a group of formula 10

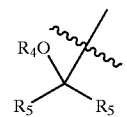

wherein $R_4$ and each $R_5$ independently are an alkyl group, a cycloalkyl group, a heterocycloalkyl group, an aryl group, or a heteroaryl group; and X is OH; $OR_7$, wherein $R_7$ is alkyl or aryl; halogen; pseudohalogen; $OSO_2R_8$, wherein $R_8$ is alkyl or aryl; heteroaryl bonded through the heteroatom; or N-hydroxyheterocyclic bonded through the oxygen. The reaction of compounds 3 and 5 produces a compound of formula 4, described above. The compound according to formula 4 is then converted to the compound of formula 7, for example, by one of the methods described above.

DETAILED DESCRIPTION OF THE INVENTION

This invention relates to compounds and intermediates useful for making HIV-protease inhibitors, methods of making the compounds and intermediates, and methods of making HIV-protease inhibitors.

As mentioned above, one aspect of this invention relates to compounds that are useful (e.g., as starting materials or intermediates) for making HIV-protease inhibitors. One such group of compounds are identified in this application by formula 3, shown below:

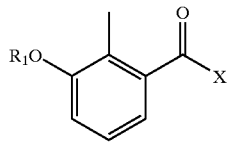

wherein $R_1$ is alkyl; cycloalkyl; heterocycloalkyl; aryl; heteroaryl; a group of formula 8

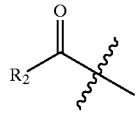

wherein $R_2$ is an alkyl group, a cycloalkyl group, a heterocycloalkyl group, O—$R_6$ (wherein $R_6$ is an alkyl group, an aralkyl group, or an aryl group); a group of formula 9

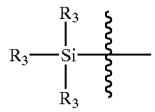

wherein each $R_3$ independently is an alkyl group, a cycloalkyl group, a heterocycloalkyl group, an aryl group, or a heteroaryl group; or a group of formula 10

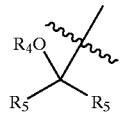

wherein $R_4$ and each $R_6$ independently are an alkyl group, a cycloalkyl group, a heterocycloalkyl group, an aryl group, or a heteroaryl group; and X is OH; $OR_7$ (wherein $R_7$ is alkyl or aryl); halogen; pseudohalogen, including azide, cyanide, isocyanate and isothiocyanate; $OSO_2R_8$ (wherein $R_8$ is alkyl or aryl); heteroaryl bonded through the heteroatom; or N-hydroxyheterocyclic, including hydroxysuccinimide or hydroxybenzotriazole ester, bonded through the oxygen, with the proviso that when $R_1$ is —$CH_3$, X cannot be —$OCH_3$ or —OH, and when $R_1$ is $CH_3C(O)$—, X cannot be —OH; and to pharmaceutically acceptable salts and solvates thereof. Preferably X is a halogen, particularly, Cl.

The present invention also is directed to novel compounds of formula 2

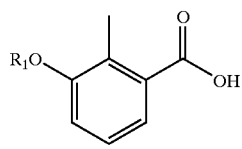

wherein $R_1$ is a $C_2$ to $C_8$ alkyl group; a cycloalkyl group; a heterocycloalkyl group; an aryl group; a heteroaryl group; a group of formula 8

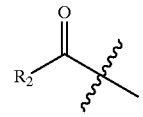

wherein $R_2$ is a $C_2$ to $C_8$ alkyl group, a cycloalkyl group, a heterocycloalkyl group, O—$R_6$ (wherein $R_6$ is an alkyl group, an aralkyl group, or an aryl group); a group of formula 9

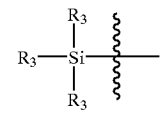

wherein each $R_3$ independently is an alkyl group, a cycloalkyl group, a heterocycloalkyl group, an aryl group, or a heteroaryl group; or a group of formula 10

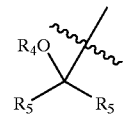

wherein $R_4$ and each $R_5$ independently are an alkyl group, a cycloalkyl group, a heterocycloalkyl group, an aryl group, or a heteroaryl group; and to pharmaceutically acceptable salts and solvates thereof.

When $R_1$ is a group of formula 8 where $R_2$ is alkyl, $R_1$ can be, for example, acetate, propanoate, butanoate, pivaloate, or any related alkyl ester or mixed carbonate with a group such as benzyl. Other examples of $R_1$ groups where $R_1$ is a group of formula 8 include esters of aromatic and heteroaromatic acids, such as benzoate, substituted benzoate, 1- or 2-naphthoate or substituted 1- or 2-naphthoate, or a substituted 5- or 6-membered heteroaromatic ester. Examples of $R_1$ groups where $R_1$ is an alkyl include methyl, substituted methyl, ethyl, propyl, and butyl. Examples of $R_1$ when $R_1$ is a silyl ether of formula 9 include trimethylsilyl, t-butyldimethylsilyl, triisopropylsilyl, triphenylsilyl, and silyl ethers where the alkyl groups $R_3$ are some combination of simple alkyl and aryl groups. Examples of $R_1$ where $R_1$ is part of an acetal or ketal of formula 10 include acetonide, cyclohexylidene ketal, benzylidene acetal, 2-methoxyethoxyethyl acetal, and related acetals and ketals where $R_4$ and $R_5$ are alkyl, cycloalkyl, heterocycloalkyl, aryl, or heteroaryl. In certain preferred compounds of formulae 2 and 3, and in pharmaceutically acceptable salts and solvates thereof, $R_1$ is —$C(O)CH_3$; alternatively expressed, $R_2$ in a group of formula 8 is $CH_3$.

The present invention is further directed to, various methods of making compounds of formulae 2, 3, 4 (nelfinavir free base), and 7 (nelfinavir mesylate), as described above. Other methods of preparing nelfinavir free base using compounds of formulae 2 and 3 are described in U.S. patent application Ser. No. 08/708,607, filed Sep. 5, 1996, which application also is entirely incorporated herein by reference. Other methods of using compounds of Formulae 2 and 3 are disclosed in JP 95-248183 and JP 95-248184, each of which is entirely incorporated herein by reference.

As used in the present application, the following definitions apply:

The term "alkyl" as used herein refers to substituted or unsubstituted, straight or branched chain groups, preferably, having one to eight, more preferably having one to six, and most preferably having from one to four carbon atoms. The term "$C_1$–$C_6$ alkyl" represents a straight or branched alkyl chain having from one to six carbon atoms. Exemplary $C_1$–$C_6$ alkyl groups include methyl, ethyl, n-propyl, isopropyl, butyl, isobutyl, sec-butyl, t-butyl, pentyl, neopentyl, hexyl, isohexyl, and the like. The term "$C_1$–$C_6$ alkyl" includes within its definition the term "$C_1$–$C_4$ alkyl."

The term "cycloalkyl" represents a substituted or unsubstituted, saturated or partially saturated, mono- or poly-carbocyclic ring, preferably having 5–14 ring carbon atoms. Exemplary cycloalkyls include monocyclic rings having from 3–7, preferably 3–6, carbon atoms, such as cyclopropyl, cyclobutyl, cyclopentyl, cyclohexyl, cycloheptyl, and the like. Exemplary cycloalkyls are $C_5$–$C_7$ cycloalkyls, which are saturated hydrocarbon ring structures containing from five to seven carbon atoms.

The term "aryl" as used herein refers to an aromatic, monovalent monocyclic, bicyclic, or tricyclic radical containing 6, 10, 14, or 18 carbon ring atoms, which may be unsubstituted or substituted, and to which may be fused one or more cycloalkyl groups, heterocycloalkyl groups, or heteroaryl groups, which themselves may be unsubstituted or substituted by one or more suitable substituents. Illustrative examples of aryl groups include, but are not limited to, phenyl, naphthyl, anthryl, phenanthryl, fluoren-2-yl, indan-5-yl, and the like.

The term "halogen" represents chlorine, fluorine, bromine, or iodine. The term "halo" represents chloro, fluoro, bromo, or iodo.

The term "carbocycle" represents a substituted or unsubstituted aromatic or a saturated or a partially saturated 5–14 membered monocyclic or polycyclic ring, which is substituted or unsubstituted, such as a 5- to 7-membered monocyclic or 7- to 10-membered bicyclic ring, wherein all the ring members are carbon atoms.

A "heterocycloalkyl group" is intended to mean a non-aromatic, monovalent monocyclic, bicyclic, or tricyclic radical, which is saturated or unsaturated, containing 3, 4, 5, 6, 7. 8, 9, 10, 11, 12, 13, 14, 15, 16, 17, or 18 ring atoms, and which includes 1, 2, 3, 4, or 5 heteroatoms selected from nitrogen, oxygen, and sulfur, wherein the radical is unsubstituted or substituted, and to which may be fused one or more cycloalkyl groups, aryl groups, or heteroaryl groups, which themselves may be unsubstituted or substituted. Illustrative examples of heterocycloalkyl groups include, but are not limited to, azetidinyl, pyrrolidyl, piperidyl, piperazinyl, morpholinyl, tetrahydro-2H-1,4-thiazinyl, tetrahydrofuryl, dihydrofuryl, tetrahydropyranyl, dihydropyranyl, 1,3-dioxolanyl, 1,3-dioxanyl, 1,4-dioxanyl, 1,3-oxathiolanyl, 1,3-oxathianyl, 1,3-dithianyl, azabicylo[3.2.1]octyl, azabicylo[3.3.1]nonyl, azabicylo[4.3.0]nonyl, oxabicylo[2.2.1]heptyl, 1,5,9-triazacyclododecyl, and the like.

A "heteroaryl group" is intended to mean an aromatic monovalent monocyclic, bicyclic, or tricyclic radical containing 5, 6, 7, 8, 9, 10, 11, 12, 13, 14, 15, 16, 17, or 18 ring atoms, including 1, 2, 3, 4, or 5 heteroatoms selected from nitrogen, oxygen, and sulfur, which may be unsubstituted or substituted, and to which may be fused one or more cycloalkyl groups, heterocycloalkyl groups, or aryl groups, which themselves may be unsubstituted or substituted. Illustrative examples of heteroaryl groups include, but are not limited to, thienyl, pyrrolyl, imidazolyl, pyrazolyl, furyl, isothiazolyl, furazanyl, isoxazolyl, thiazolyl, pyridyl, pyrazinyl, pyrimidinyl, pyridazinyl, triazinyl, benzo[b]thienyl, naphtho[2,3-b]thianthrenyl, isobenzofuranyl, chromenyl, xanthenyl, phenoxathienyl, indolizinyl, isoindolyl, indolyl, indazolyl, purinyl, isoquinolyl, quinolyl, phthalazinyl, naphthyridinyl, quinoxyalinyl, quinzolinyl, benzothiazolyl, benzimidazolyl, tetrahydroquinolinyl, cinnolinyl, pteridinyl, carbazolyl, beta-carbolinyl, phenanthridinyl, acridinyl, perimidinyl, phenanthrolinyl, phenazinyl, isothiazolyl, phenothiazinyl, and phenoxazinyl.

The term "acyl" represents $L_6C(O)L_4$, wherein $L_6$ is a single bond, —O, or —N, and further wherein $L_4$ is preferably alkyl, amino, hydroxyl, alkoxyl, or hydrogen. The alkyl, amino, and alkoxyl groups optionally can be substituted. An exemplary acyl is a $C_1$–$C_4$ alkoxycarbonyl, which is a straight or branched alkoxyl chain having from one to four carbon atoms attached to a carbonyl moiety. Exemplary $C_1$–$C_4$ alkoxycarbonyl groups include methoxycarbonyl, ethoxycarbonyl, propoxycarbonyl, isopropoxycarbonyl, butoxycarbonyl, and the like. Another exemplary acyl is a carboxy wherein $L_6$ is a single bond and $L_4$ is alkoxyl, hydrogen, or hydroxyl. A further exemplary acyl is N—($C_1$–$C_4$)alkylcarbamoyl ($L_6$ is a single bond and $L_4$ is an amino), which is a straight or branched alkyl chain having from one to four carbon atoms attached to the nitrogen atom of a carbamoyl moiety. Exemplary N—($C_1$–$C_4$) alkylcarbamoyl groups include N-methylcarbamoyl, N-ethylcarbamoyl, N-propylcarbamoyl, N-isopropylcarbamoyl, N-butylcarbamoyl, and N-t-butylcarbamoyl, and the like. Yet another exemplary acyl is N,N-di($C_1$–$C_4$)alkylcarbamoyl, which has two straight or branched alkyl chains, each having from one to four carbon atoms attached to the nitrogen atom of a carbamoyl moiety. Exemplary N,N-di($C_1$–$C_4$)alkylcarbamoyl groups include N,N-dimethylcarbamoyl, N,N-,ethylmethylcarbamoyl, N,N-methylpropylcarbamoyl, N,N-ethylisopropylcarbamoyl, N,N-butylmethylcarbamoyl, N,N-sec-butylethylcarbamoyl, and the like.

Suitable protecting groups are recognizable to those skilled in the art. Examples of suitable protecting groups can be found in T. Green & P. Wuts, *Protective Groups in Organic Synthesis* (2d ed. 1991), which is incorporated herein by reference.

The term "aralkyl" as used herein refers to any substituted or unsubstituted group that is $sp^3$ hybridized at the point of attachment that also possesses an aromatic ring or rings with that group.

The term "pseudohalogen" as used herein refers to azides, cyanides, isocyanates, and isothiocyanates.

The term "N-hydroxyheterocyclic" as used herein refers to substituted and unsubstituted groups having an oxygen atom at the point of attachment that is also bonded to the nitrogen of a nitrogen heterocyclic ring or ring system. Examples of such groups include:

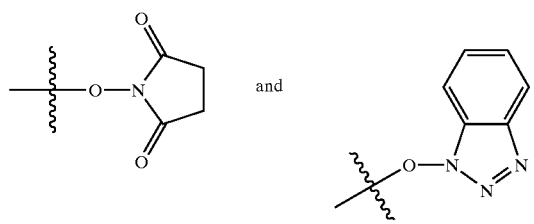

The term "alkyl ester" as used herein refers to ester groups where the group attached to the esterifying oxygen is an alkyl group.

The term "mixed carbonate" as used herein refers to compounds containing the functional group

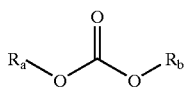

where $R_a$ and $R_b$ independently are alkyl, aryl, or aralkyl groups.

The term "ester of an aromatic or heteroaromatic acid" as used herein refers to carboxylic acids wherein the carboxyl group is attached directly to a substituted or unsubstituted aromatic or heteroaromatic ring, such as benzoic acid or 2-furoic acid.

The term "DABCO" as used herein refers to the reagent 1,4-diazabicyclo[2.2.2]octane.

The term "DBN" as used herein refers to the reagent 1,5-diazabicyclo[4.3.0]non-5-ene.

The term "DBU" as used herein refers to the reagent 1,8-diazabicyclo[5.4.0]undec-7-ene.

The term "silyl ether" as used herein refers to the group:

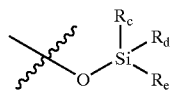

wherein $R_c$, $R_d$, and $R_e$ independently are alkyl, aryl or aralkyl groups.

The term "perfluoralkanesulfonate" as used herein refers to alkane sulfonate esters wherein one or more of the hydrogens are replaced by fluorines.

The term "vinyl alkyl ether" as used herein refers to ether groups where an alkyl group and a substituted or unsubstituted olefin-containing group are bonded to the ethereal oxygen, and the olefin-containing group is bonded to the ethereal oxygen at one of the doubly-bonded carbons.

The term "arylsufonic acid" as used herein refers to groups of formula:

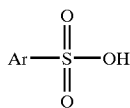

wherein Ar is a substituted or unsubstituted aromatic ring.

The term "leaving group" as used herein refers to any group that departs from a molecule in a substitution reaction by breakage of a bond. Examples of leaving groups include, but are not limited to, halides, arenesulfonates, alkylsulfonates, and triflates.

The term "arenesulfonate" as used herein refers to any substituted or unsubstituted group that is an ester of an arylsulfonic acid.

The term "alkyl or aryl carbodiimides" as used herein refers to any reagent of formula $R_f$—N=C=N—$R_g$, wherein $R_f$ and $R_g$ independently are aryl, alkyl, or aralkyl.

The term "DMF" as used herein refers to the solvent N,N-dimethylformamide.

The term "NMP" as used herein refers to the solvent N-methyl-2-pyrolidinone.

The term "THF" as used herein refers to the solvent tetrahydrofuran.

The term "alkyl thiolates" as used herein refers to substituted or unsubstituted compounds that are metal salts of alkanethiols.

The term "trialkylsilyl halide" as used herein refers to compounds having a silicon that holds 3 alkyl groups that may be the same or different.

The term "hydrogenolysis" as used herein refers to a reaction in which a single bond is broken and hydrogens become bonded to the atom's that were formerly bonded.

Examples of substituents for alkyl and aryl include mercapto, thioether, nitro ($NO_2$), amino, aryloxyl, halogen, hydroxyl, alkoxyl, and acyl, as well as aryl, cycloalkyl, and saturated and partially saturated heterocycles. Examples of substituents for cycloalkyl include those listed above for alkyl and aryl, as well as aryl and alkyl.

Exemplary substituted aryls include a phenyl or naphthyl ring substituted with one or more substituents, preferably one to three substituents independently selected from halo; hydroxy; morpholino($C_1$–$C_4$)alkoxy carbonyl; pyridyl ($C_1$–$C_4$)alkoxycarbonyl; halo ($C_1$–$C_4$)alkyl; $C_1$–$C_4$ alkyl; $C_1$–$C_4$alkoxy; carboxy; $C_1$–$C_4$ alkoxycarbonyl; carbamoyl; N—($C_1$–$C_4$)alkylcarbamoyl; amino; $C_1$–$C_4$alkylamino; di($C_1$–$C_4$)alkylamino; or a group of the formula —$(CH_2)_a$—$R^7$ where a is 1, 2, 3, or 4, and $R^7$ is hydroxy, $C_1$–$C_4$ alkoxy, carboxy, $C_1$–$C_4$ alkoxycarbonyl, amino, carbamoyl, $C_1$–$C_4$ alkylamino, or di($C_1$–$C_4$)alkylamino.

Another substituted alkyl is halo($C_1$–$C_4$)alkyl, which represents a straight or branched alkyl chain having from one to four carbon atoms with 1–3 halogen atoms attached to it. Exemplary halo($C_1$–$C_4$)alkyl groups include chloromethyl, 2-bromoethyl, 1-chloroisopropyl, 3-fluoropropyl, 2,3-dibromobutyl, 3-chloroisobutyl, iodo-t-butyl, trifluoromethyl, and the like.

Another substituted alkyl is hydroxy($C_1$–$C_4$)alkyl, which represents a straight or branched alkyl chain having from one to four carbon atoms with a hydroxy group attached to it. Exemplary hydroxy($C_1$–$C_4$)alkyl groups include hydroxymethyl, 2-hydroxyethyl, 3-hydroxypropyl, 2-hydroxyisopropyl, 4-hydroxybutyl, and the like.

Yet another substituted alkyl is $C_1$–$C_4$ alkylthio($C_1$–$C_4$) alkyl, which is a straight or branched $C_1$–$C_4$ alkyl group with a $C_1$–$C_4$ alkylthio group attached to it. Exemplary $C_1$–$C_4$ alkylthio($C_1$–$C_4$)alkyl groups include methylthiomethyl, ethylthiomethyl, propylthiopropyl, sec-butylthiomethyl, and the like.

Yet another exemplary substituted alkyl is heterocycle ($C_1$–$C_4$)alkyl, which is a straight or branched alkyl chain having from one to four carbon atoms with a heterocycle attached to it. Exemplary heterocycle($C_1$–$C_4$)alkyls include pyrrolylmethyl, quinolinylmethyl, 1-indolylethyl, 2-furylethyl, 3-thien-2-ylpropyl, 1-imidazolylisopropyl, 4-thiazolylbutyl, and the like.

Yet another substituted alkyl is aryl($C_1$–$C_4$)alkyl, which is a straight or branched alkyl chain having from one to four carbon atoms with an aryl group attached to it. Exemplary aryl($C_1$–$C_4$)alkyl groups include phenylmethyl, 2-phenylethyl, 3-naphthyl-propyl, 1-naphthylisopropyl, 4-phenylbutyl, and the like.

The heterocycloalkyls and heteroaryls can, for example, be substituted with 1, 2, or 3 substituents independently selected from halo; halo($C_1$–$C_4$)alkyl; $C_1$–$C_4$ alkyl; $C_1$–$C_4$ alkoxy; carboxy; $C_1$–$C_4$ alkoxycarbonyl; carbamoyl; N—($C_1$–$C_4$)alkylcarbamoyl; amino; $C_1$–$C_4$alkylamino; di($C_1$–$C_4$)alkylamino; or a group having the structure —$(CH_2)_a$—$R^7$ where a is 1, 2, 3, or 4, and $R^7$ is hydroxy, $C_1$–$C_4$ alkoxy, carboxy, $C_1$–$C_4$ alkoxycarbonyl, amino, carbamoyl, $C_1$–$C_4$alkylamino, or di($C_1$–$C_4$)alkylamino.

Examples of substituted heterocycloalkyls include, but are not limited to, 3-N-t-butyl carboxamide decahydroisoquinolinyl and 6-N-t-butyl carboxamide octahydro-thieno[3,2-c]pyridinyl. Examples of substituted heteroaryls include, but are not limited to, 3-methylimidazolyl, 3-methoxypyridyl, 4-chloroquinolinyl, 4-aminothiazolyl, 8-methylquinolinyl, 6-chloroquinoxalinyl, 3-ethylpyridyl, 6-methoxybenzimidazolyl, 4-hydroxyfuryl, 4-methylisoquinolinyl, 6,8-dibromoquinolinyl, 4,8- dimethylnaphthyl, 2-methyl-1,2,3,4-tetrahydroisoquinolinyl, N-methyl-quinolin-2-yl, 2-t-butoxycarbonyl-1,2,3,4-isoquinolin-7-yl, and the like.

A "pharmaceutically acceptable solvate" is intended to mean a solvate that retains the biological effectiveness and properties of the biologically active components of compounds of formulae 2 and 3.

Examples of pharmaceutically acceptable solvates include, but are not limited to, compounds prepared using water, isopropanol, ethanol, methanol, DMSO, ethyl acetate, acetic acid, or ethanolamine.

In the case of solid formulations, it is understood that the inventive compounds can exist in different forms, such as stable and metastable crystalline forms and isotropic and amorphous forms, all of which are intended to be within the scope of the present invention.

A "pharmaceutically acceptable salt" is intended to mean those salts that retain the biological effectiveness and properties of the free acids and bases and that are not biologically or otherwise undesirable.

Examples of pharmaceutically acceptable salts include, butare not limited to, sulfates, pyrosulfates, bisulfates, sulfites, bisulfites, phosphates, monohydrogenphosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, xylenesulfonates, phenylacetates, phenylpropionates, phenylbutyrates, citrates, lactates, y-hydroxybutyrates, glycolates, tartrates, methanesulfonates, propanesulfonates, naphthalene-1-sulfonates, naphthalene-2-sulfonates, and mandelates.

If the inventive compound is a base, the desired salt can be prepared by any suitable method known in the art, including treatment of the free base with an inorganic acid, such as hydrochloric acid; hydrobromic acid; sulfuric acid; nitric acid; phosphoric acid; and the like, or with an organic acid, such as acetic acid; maleic acid; succinic acid; mandelic acid; fumaric acid; malonic acid; pyruvic acid; oxalic acid; glycolic acid; salicylic acid; pyranosidyl acids such as glucuronic acid and galacturonic acid; alpha-hydroxy acids such as citric acid and tartaric acid; amino acids such as aspartic acid and glutamic acid; aromatic acids such as benzoic acid and cinnamic acid; sulfonic acids such a p-toluenesulfonic acid or ethanesulfonic acid; or the like.

If the inventive compound is an acid, the desired salt can be prepared by any suitable method known in the art, including treatment of the free acid with an inorganic or organic base, such as an amine (primary, secondary, or tertiary), an alkali metal or alkaline earth metal hydroxide, or the like. Illustrative examples of suitable salts include organic salts derived from amino acids such as glycine and arginine; ammonia; primary, secondary, and tertiary amines; and cyclic amines such as piperidine, morpholine, and piperazine, and inorganic salts derived from sodium, calcium, potassium, magnesium, manganese, iron, copper, zinc, aluminum, and lithium.

All inventive compounds that contain at least one chiral center can exist as single stereoisomers, racemates, and/or mixtures of enantiomers and/or diastereomers. All such single stereoisomers, racemates, and mixtures thereof are intended to be within the scope of the present invention. Preferably, the compounds of the present invention are used in a form that contains at least 90% of a single isomer (80% enantiomeric or diastereomeric excess), more preferably at least 95% (90% e.e. or d.e.), even more preferably at least 97.5% (95% e.e. or d.e.), and most preferably at least 99% (98% e.e. or d.e.). Compounds identified herein as single stereoisomers are meant to describe compounds used in a form that contains at least 90% of a single isomer.

The inventive compounds can be prepared by the novel methods of the present invention, which are described in detail below. Additionally, these compounds can be used to prepare nelfinavir free base and nelfinavir mesylate according to the inventive methods described below.

A reaction scheme for the conversion of 3-hydroxy-2-methylbenzoic acid derivatives to nelfinavir free base is as follows:

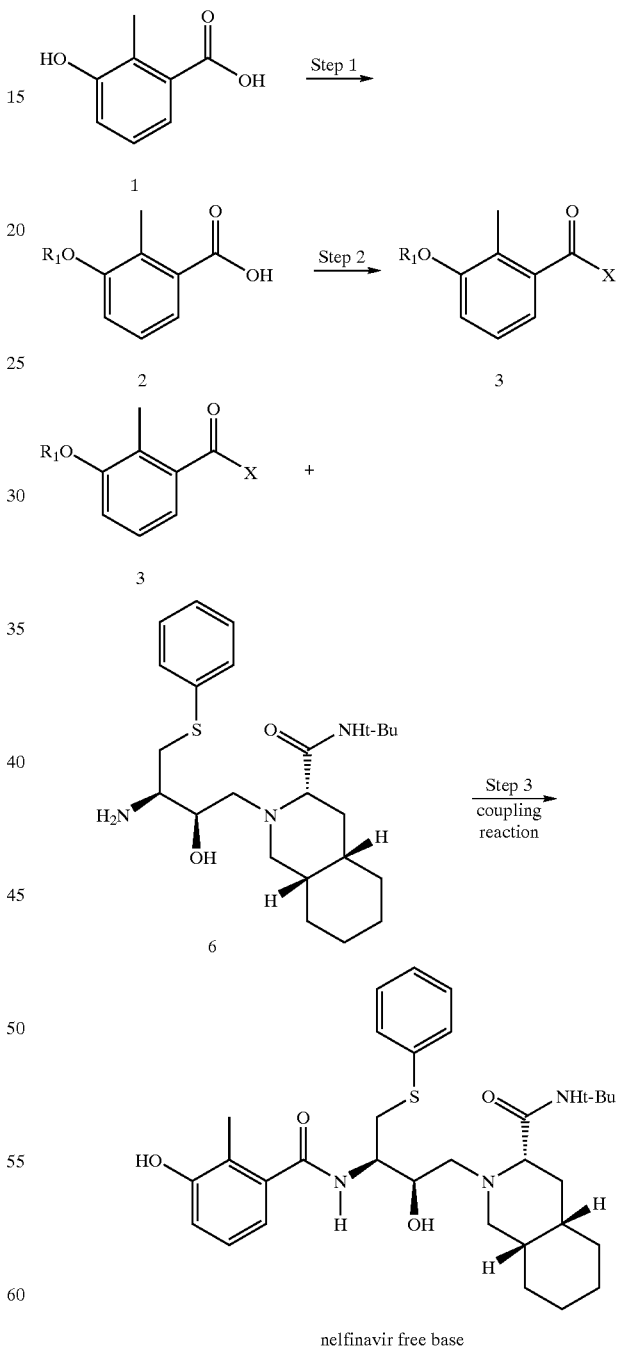

The acid 1 is commercially available from Lancaster Labs and Sugai Chemical Industries, Ltd. in Japan. The acid 1 also can be obtained according to the procedure described in U.S. Pat. No. 5,484,926, for the Preparation of 9C.

When $R_1$ is an acyl group or an ester of an aromatic or heteroaromatic acid, $R_1$ can be installed onto 3-hydroxy-2-methylbenzoic acid (Step 1) using the corresponding acyl halides or anhydrides in typical organic solvents for these types of reactions, such as halogenated solvents, ethers, and hydrocarbons accompanied by a base. Such bases typically are inorganic bases, such as metal hydroxides, bicarbonates, and carbonates, or organic bases, such as amines like triethylamine, diethylamine, diethyl isopropylamine, DABCO, or related di- or trialkylamines, as well as amidine bases like DBU and DBN. These reactions typically are run anywhere from below room temperature to approximately 100° C. Alternatively, the esterification can be catalyzed by acids such as sulfuric acid when used in conjunction with anhydrides.

When $R_1$ is an ether group, $R_1$ can be installed using conditions that utilize the corresponding $R_1$ group bonded to a leaving group, which is subsequently displaced. These reactions generally are performed in most common organic solvents such as THF, diethyl ether, dioxane, methyl t-butyl ether, or other ethers; esters such as ethyl, methyl, and isopropyl acetate; halogenated solvents such as halogenated methanes and ethanes, chlorobenzene, and other halogenated benzenes; nitriles such acetonitrile and propionitrile; lower alcohols such as ethanol, isopropanol, t-butanol, and related alcohols; and polarorganic solvents such as dimethyiformamide, dimethylsulfoxide, N-methyl-2-pyrolidinone, and related amide-containing solvents. A base usually accompanies such a process. The bases typically are inorganic, such as metal hydroxides, bicarbonates, and carbonates, or organic, such as amines like triethylamine, diethylamine, diethyl isopropylamine, DABCO, or related di- or trialkylamines, as well as amidine bases like DBU and DBN. These reactions typically are run anywhere from below room temperature to approximately 100° C.

When $R_1$ is a silyl ether, it can be installed using the corresponding silyl halides or perfluoralkanesulfonates in most common organic solvents such as THF, diethyl ether, dioxane, methyl t-butyl ether, or other ethers; esters such as ethyl, methyl, and isopropyl acetate; halogenated solvents such as halogenated methanes and ethanes, chlorobenzene, and other halogenated benzenes; nitriles such acetonitrile and propionitrile; and polar organic solvents such as dimethylformamide, N-methyl-2-pyrolidinone, and related amide-containing solvents. A base usually accompanies such a process. The bases typically are inorganic bases, such as metal hydroxides, bicarbonates, and carbonates, or organic bases, such as amines like triethylamine, diethylamine, diethyl isopropylamine, DABCO, or related di- or trialkylamines, as well as amidine bases like DBU and DBN.

When $R_1$ is part of an acetal or ketal group, $R_1$ can be installed by alkylation with the corresponding α-haloether in a manner similar to other alkyl halides as described above. Alternatively, acid-promoted addition of 3-hydroxy-2-methylbenzoic acid to the corresponding vinyl alkyl ether can be used. These reactions are promoted by both organic acids (such as p-toluenesulfonic and related alkyl and arylsulfonic acids, trifluoroacetic acid and related organic carboxylic acids with a pK of less than 2) and inorganic acids (such as sulfuric, hydrochloric, phosphoric, and nitric acids).

The group X is installed in Step 2 by reaction of the carboxylic acid derivative 2. The acyl halides of formula 3 can be prepared using inorganic halogenating agents such as thionyl chloride or bromide, phosphorus trichloride or -bromide, phosphorus pentachloride or bromide, or organic agents such as oxalyl chloride or trichlorisocyanuric acid. This process can be catalyzed by DMF or a related alkyl amide.

Esters of formula 3 can be prepared in a variety of ways starting from the acid chloride (compounds of formula 3) by combination with the desired alcohol in the presence of an organic or inorganic base stated previously. Alternatively, the ester can be produced by acid-promoted esterification in the presence of the desired alcohol. The sulfonates usually are made by reaction of the carboxylic acid derivatives (compounds of formula 2) with alkyl or arylsulfonyl chlorides in the presence of an organic amine base such as triethylamine in a non-polar solvent at temperatures below 0° C. The pseudohalogen derivatives generally are made from the acid halides (compounds of formula 3) by reaction with inorganic pseudohalide in the presence of a base. The heteroaryl derivatives (compounds of formula 2) also are made from the acid halides of formula 3 utilizing the specific heteroaryl compound in the presence of an amine base in a non-polar solvent. The N-hydroxyheterocyclic derivatives can be made from the acid halides of formula 3 as above and can also be generated using alkyl or aryl carbodiimides and an amine base as condensing agents.

The coupling of compound 3 to amine 6 (Step 3) can be carried out in a variety of ways, depending on the identity of X. When a free acid is used (X=OH), the coupling can be performed using carbodiimide based methods utilizing any of the common reagents of this class including dicyclohexylcarbodiimide or related dialkylcarbodiimides, EDC (salts of 1-(3-dimethylaminopropyl)-3-ethylcarbodiimide) or related water soluble reagents along with an organic amine base in polar organic solvents such as dioxane, DMF, NMP, and acetonitrile in the presence of an N-hydroxyheterocyclic including hydroxysuccinimide or N-hydroxybenzotrazole ester. When X is a halogen or pseudohalogen, the coupling can be performed in most common organic solvents such as THF; diethyl ether, dioxane, methyl t-butyl ether, or other ethers; acetone, cyclohexanone, methyl isobutylketone and other ketones; esters such as ethyl, methyl, and isopropyl acetate; halogenated solvents such as halogenated methanes and ethanes; chlorobenzene and other halogenated benzenes; nitriles such acetonitrile and propionitrile; lower alcohols such as ethanol, isopropanol, t-butanol, and related alcohols; and polar organic solvents such as dimethylformamide, dimethylsulfoxide, N-methyl-2-pyrolidinone, and related amide-containing solvents. A base frequently is used and can be any of a number of inorganic bases (such as metal hydroxides, bicarbonates, and carbonates) or organic bases (such as amines like. triethylamine, diethylamine, diethyl isopropylamine, DABCO, or related di- or trialkylamines, as well as amidine bases like DBU and DBN).

Protecting group removal is accomplished using any of the standard methods for deprotecting a particular class of protecting group. Esters and carbonates usually are removed with aqueous or alcoholic solutions of inorganic bases, such as metal hydroxides, carbonates, and bicarbonates, at ambient temperatures up to 100° C. Ethers are deprotected using boron- based Lewis acidic compounds such as $BBr_3$ and $BCl_3$, alkyl thiolates, or trialkylsilyl halides. Either ether or carbonate protecting groups that contain benzyl groups bonded to heteroatoms can be removed by hydrogenolysis with a palladium or platinum catalyst. Acetal-based protecting groups can be removed under aqueous or alcoholic acidic conditions, promoted by Lewis acids such as transition metal halides or halides of the Group 3 metals, or by protic organic acids (such as p-toluenesulfonic and related alkyl and arylsulfonic acids, trifluoroacetic acid and related organic carboxylic acids with a pK of less than 2) and inorganic acids (such as sulfuric, hydrochloric, phosphoric, and nitric acids). Silylether protecting group removal can be accomplished by aqueous or alcoholic acid or base or by fluoride ion promoted desilylation by use of inorganic fluoride sources such as potassium or cesium fluoride or by tetralkylammonium fluoride salts.

Nelfinavir mesylate can be prepared from 3-acetoxy-2-methylbenzoyl chloride (acid chloride). The acid chloride can be prepared from the corresponding 3-hydroxy-2-methylbenzoic acid in the following two step procedure:

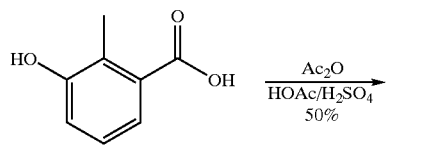

1

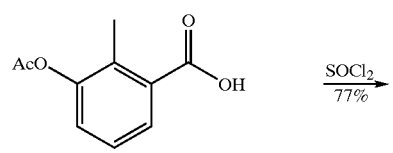

3-acetoxy-2-methylbenzonic acid

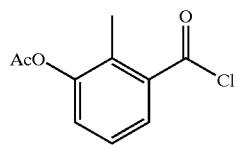

3-acetoxy-2-methylbenzonyl chloride

In the production of the acid chloride, the acid 1 is converted to the acetoxy acid (a compound of formula 2), which is treated with thionyl chloride to give 3-acetoxy-2-methylbenzoyl chloride in good yield.

The acid chloride then can be coupled to the amine 6 under classical conditions resulting in the production of nelfinavir free base as follows:

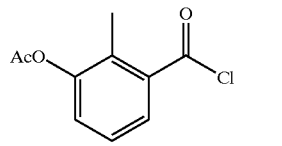

3-acetoxy-2-methylbenzoyl chloride

+

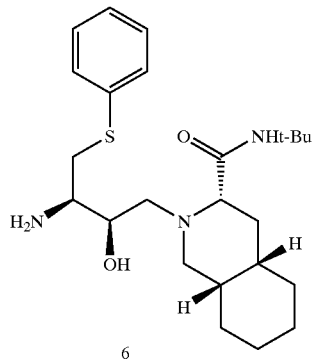

6 coupling reaction →

-continued

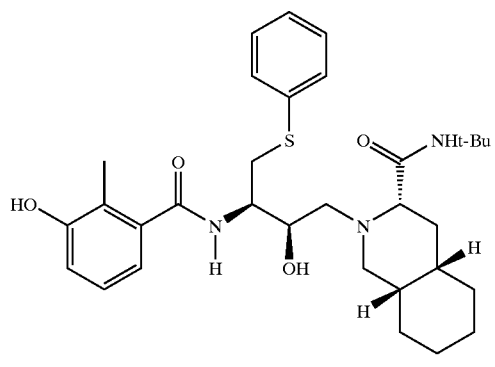

nelfinavir free base

The acid chloride is treated with the amine 6 in the presence of triethylamine in THF at ambient temperature for 30 minutes followed by an aqueous basic hydrolysis of the acetate group to give nelfinavir free base. The free base can be converted to nelfinavir mesylate by methods described in more detail below.

Preparation of Nelfinavir Free Base From 3-Acetoxy-2-Methylbenzoic Chloride

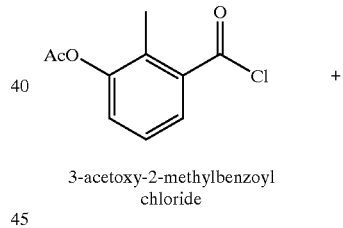

3-acetoxy-2-methylbenzoyl chloride

+

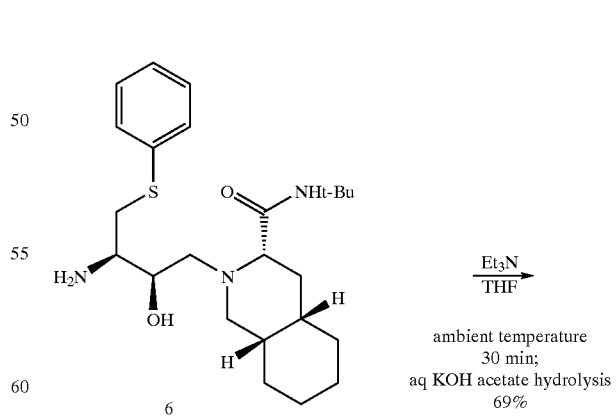

6

$\xrightarrow{\text{Et}_3\text{N}}{\text{THF}}$ ambient temperature
30 min;
aq KOH acetate hydrolysis
69%

25

-continued

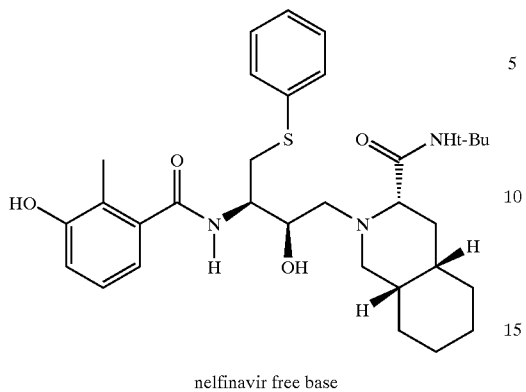

nelfinavir free base

Summary of the Process

To obtain 3-acetoxy-2-methylbenzoyl chloride, 3-hydroxy-2-methylbenzoic acid was slurried in acetic acid with acetic anhydride and catalytic sulfuric acid. Acetylation of the hydroxy group was complete within two hours at ambient temperature. After complete reaction, the resulting slurry was poured into water, and the product was isolated by filtration. The wet cake was reslurried in water, isolated by filtration, and dried under vacuum. Product was obtained in 80–90% yield with an apparent purity of 89–92% by HPLC. Crude, dry 3-acetoxy-2-methylbenzoic acid was dissolved in four volumes of ethyl acetate with refluxing. The resulting solution was cooled to <70° C., and five volumes of hexanes were added. The mixture was returned to reflux and then cooled to <10° C. for 1 hour. The slurry was filtered, rinsing the reactor with filtrate. The product was dried under vacuum. Recrystallization improved the HPLC UV apparent purity from 89–92% to >98%. The single largest impurity dropped from 4–5% to ~0.5%. The product was 3-acetoxy-2-methylbenzoic acid.

3-Acetoxy-2-methylbenzoic acid was slurried in methyl-t-butyl ether (MTBE) and treated with 1.2 equivalents of thionyl chloride and catalytic dimethylformamide. After three hours at ambient temperatures, the reaction was complete, giving a brown soluton. Solvent (MTBE) was removed by vacuum distillation. Residual thionyl chloride was removed by addition of toluene followed by vacuum distillation. The resulting 3-acetoxy-2-methylbenzoyl chloride was isolated either directly as an oil or by crystallization from two volumes of heptane at <10° C. Product was obtained in >100% yield when isolated as an oil and 82–85% yield when crystallized from heptane.

To obtain compound 6 for the coupling, a compound of formula 5 (made as described below) was refluxed in a mixture of ethanol and aqueous NaOH to cleave the CBZ protecting group forming a compound of formula 6. Water and HCl were added to dissolve the $Na_2CO_3$ and neutralize excess NaOH, giving a biphasic mixture. The mixture was cooled, and the lower aqueous layer was removed. Triethylamine was added followed by a solution of 3-acetoxy-2-methylbenzoyl chloride in tetrahydrofuran to give an acetate of the compound of formula 4. Aqueous NaOH was added, and the mixture was heated to reflux to give a compound of formula 4. The mixture was concentrated at atmospheric pressure to remove tetrahydrofuran, triethylamine, and most of the ethanol. The mixture was added to a heated solution of water and glacial acetic acid to precipitate the product. The pH was adjusted with additional acid, and the solids were filtered off while hot. The wet cake was rinsed with hot water and dried to give crude nelfinavir free base.

26

This method is described in more detail below.

Preparation of 3-Acetoxy-2-methylbenzoic Acid

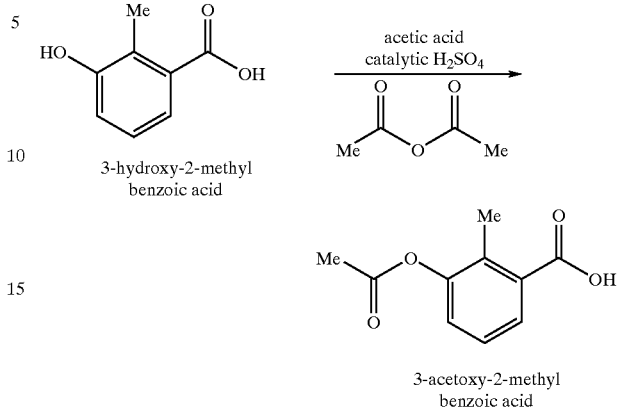

PROCEDURE

Materials

| | | | | |
|---|---|---|---|---|
| 3-hydroxy-2-methyl-benzoic acid | FW 152.15 | | 3500 g | 1.0 equiv |
| acetic acid | | | 8750 mL | |
| sulfuric acid | | | 70 mL | |
| acetic anhydride | FW 102.1 | d 1.082 | 2390 mL | 1.1 equiv |
| purified water | | | 28000 mL | |

Acetic acid (8750 mL), 3-hydroxy-2-methylbenzoic acid (3500 g), and sulfuric acid (70 mL) were charged into a 22 liter reactor. The reactor contents were stirred to give a homogeneous mixture. The mixture exothermed to 36° C. Acetic anhydride (2390 mL) was added to the mixture in the 22 L reactor. An exotherm warmed the reactor contents from 36 to 44° C. The reaction mixture was stirred at ambient temperature for two hours (reactor contents allowed to cool slowly). The reaction was tested for complete conversion of the starting material by TLC. The reaction mixture was generally a tan slurry at the completion of the reaction.

Purified water (17500 mL) was added to a 50 L extractor, and the reaction mixture from the 22 L reactor was added to this water. The 22 L reactor was rinsed into the 50 L extractor with purified water (3500 mL). The reaction mixture was vacuum filtered, washing the reactor and filter cake with purified water (3500 mL). The wet filter cake was transferred to a 50 L extractor,,and purified water (14000 mL) was added, with stirring, to obtain a homogeneous slurry. The reslurried mixture was vacuum filtered, and the reactor and filter cake were rinsed with purified water (3500 mL). The filter cake was pulled as dry as possible and then transferred to drying pans. The product was dried in a vacuum oven at 60–80° C. and ≧28 mm Hg for 12–72 hours. Theoretical yield: 4466 g. Actual weight produced: 3910 g (87.6%). HPLC assay: 89.4% or 87.7%.

Purification was achieved as follows. The crude 3-acetoxy-2-methylbenzoic acid (3910 g from above) and ethyl acetate (16.0 L) were charged to a 50 L reactor. The reactor contents were heated to reflux (77° C.) until all solids went into solution. The reactor contents were cooled to <70° C. Hexanes (19.5 L) were added to the reactor. The reactor contents were again heated to reflux (69° C.), and then the mixture was cooled to <10° C. for 1 hour. The cooled slurry from this step was vacuum filtered, and the reactor was rinsed with cold mother liquors. The filter cake was pulled as dry as possible and then transferred to drying pans. The product was dried in a vacuum oven at 60–70° C. and ≧28 mm Hg for 12–72 hours. Theoretical yield: 3910 g. Actual weight produced: 3128 g (80%). This procedure improves the HPLC UV apparent purity from 89–92% to >98%. The single largest impurity drops from 4–6% to <1% The isolated product is a tan solid. $^1$H NMR δ 8.0 (d, 1H), 7.3 (overlapping m, 2H), 2.5 (s, 3H), 2.3 (s, 3H).

Preparation of 3-Acetoxy-2-methylbenzoyl Chloride

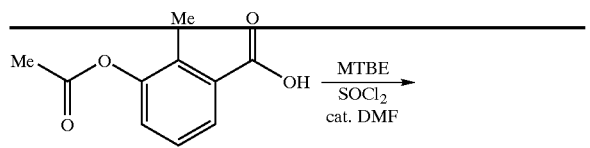

3-acetoxy-2-methyl benzoic acid

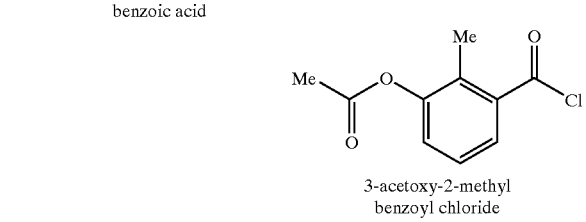

3-acetoxy-2-methyl benzoyl chloride

PROCEDURE:

| Materials | MW | d | wt | equiv. |
|---|---|---|---|---|
| 3-acetoxy-2-methylbenzoic acid | 194.19 | | 3000 g | 1.0 |
| methyl-t-butyl ether | 118.97 | | 12000 ml | |
| thionyl chloride | 118.97 | 1.638 | 1350 ml | 1.2 |
| dimethylformamide | 73.09 | 0.944 | 60 ml | 0.05 |
| toluene | | | 7500 ml | |
| heptane | | | 7500 ml | |

A 22 L reactor was purged with nitrogen and charged with recrystallized 3-acetoxy-2-methylbenzoic acid (3000 g), MTBE (12000 ml), and dimethylformamide (60 ml). The reactor contents were stirred to give a homogeneous mixture. Thionyl chloride (1350 ml) was added to the reactor. This reaction mixture was stirred at ambient temperature for 19 hours. (Generally no more than 3 hours are required for complete reaction, but the mixture can be held longer for convenience). The reaction solution was transferred to a Bochi rotovap, and the reactor was rinsed with toluene (1500 ml). The solution was concentrated as far as possible, maintaining the bath temperature at 40–50° C. Toluene (6000 ml) was added to this concentrated solution. The toluene was distilled by rotovap to drive off excess thionyl chloride. The concentrate was transferred, back to the 22 L reactor, and the Büchi flask was rinsed with heptane (6000 ml). The heptane mixture was cooled to <5° C. under nitrogen. After holding the crystallization mixture at <5° C. for >30 minutes, the mixture was filtered, and the filter cake was washed with chilled heptane (1500 ml, <5° C.). The filter cake was dried in a vacuum oven at 15–20° C. and 228 mm Hg for 24 hours, giving a tan, granular solid. Theoretical yield: 3285 g. Actual weight produced: 2704 g (82.3%). HPLC assay 97.51%; $^1$H NMR δ 8.1 (d, 1H), 7.4 (overlapping m, 2H), 2.4 (s, 6H).

Conversion of 3-Acetoxy52-methylbenzoyl Chloride and Compound 6 to Nelfinavir Free Base

REACTION SCHEME:

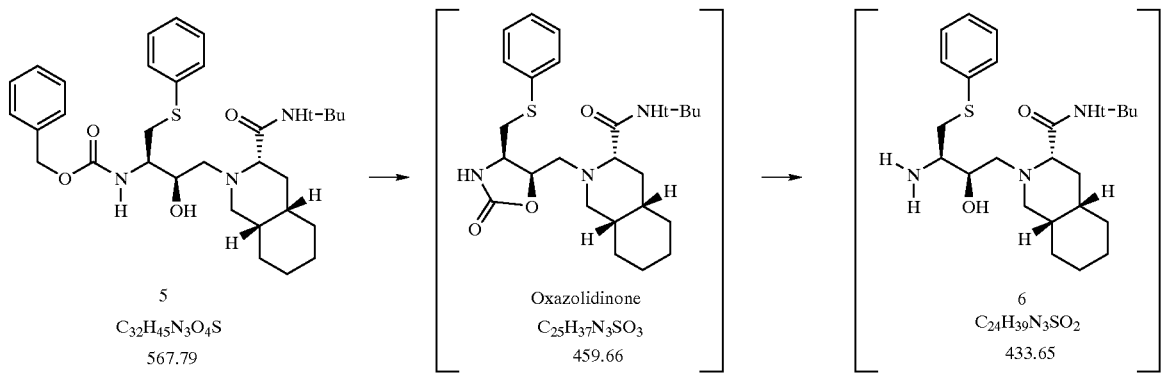

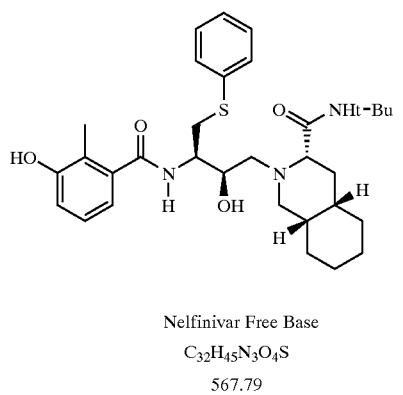

Nelfinivar Free Base
C₃₂H₄₅N₃O₄S
567.79

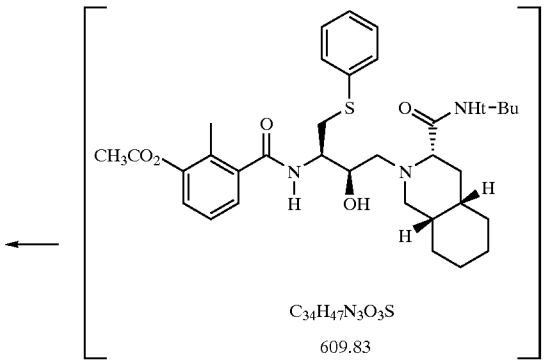

C₃₄H₄₇N₃O₃S
609.83

Step A: Conversion of Compound 5 to Compound 6.

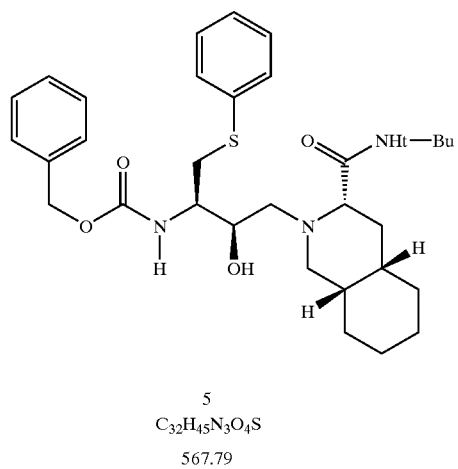

5
C₃₂H₄₅N₃O₄S
567.79

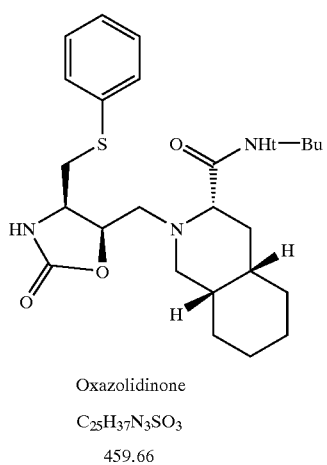

Oxazolidinone
C₂₅H₃₇N₃SO₃
459.66

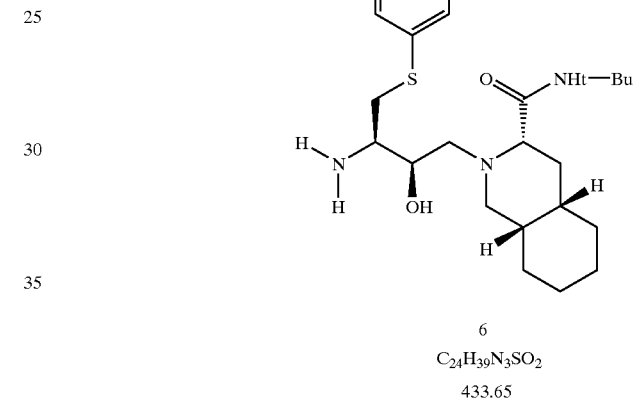

6
C₂₄H₃₉N₃SO₂
433.65

A 22 liter 3-neck round bottom flask ("RBF"), fitted with a condenser, temperature probe, and mechanical stirrer, was charged with a compound of formula 5 (1 kg. 97.7%, 1.72 mol, 1.00 eq) (which can be prepared as described below), ethanol (5 l, 95%), NaOH (280 ml, 50%, 5.33 mol. 3.1 eq), and water (2 l, DI). The mixture was stirred and heated to reflux (80–82° C.). All solids dissolved at 50° C. to give a clear yellow solution. The mixture became hazy with $Na_2CO_3$ precipitation as the reaction proceeded (Vol=8280 ml). The deprotection was monitored by HPLC. Analysis at 210 minutes showed complete consumption of the compound of formula 5, 0.95% oxazolidinone, 36% benzyl alcohol, and 62.5% of a compound of formula 6. Analysis at 300 minutes showed 0.34% oxazolidinone, 36% benzyl alcohol and 62.6% of compound of formula 6. Water (1260 ml) was added to the mixture to dissolve all solids, and the mixture was cooled to 67° C. (Vol=9540 ml). HCl (344 ml, 6 N, 2.06 mol, 1.2 eq.) was then added to the mixture. The mixture was agitated 10 minutes and then allowed to settle for 20 minutes to give two layers (Vol=9884 ml). The lower aqueous $Na_2CO_3$ layer was removed at 60° C. The volume of the aqueous cut was 365 ml, pH=14. The pH of the clear yellow upper layer was 10–10.5. The upper layer was used directly in the next step.

Step B: Conversion of Compound 6 to an Acetate of Compound 4.

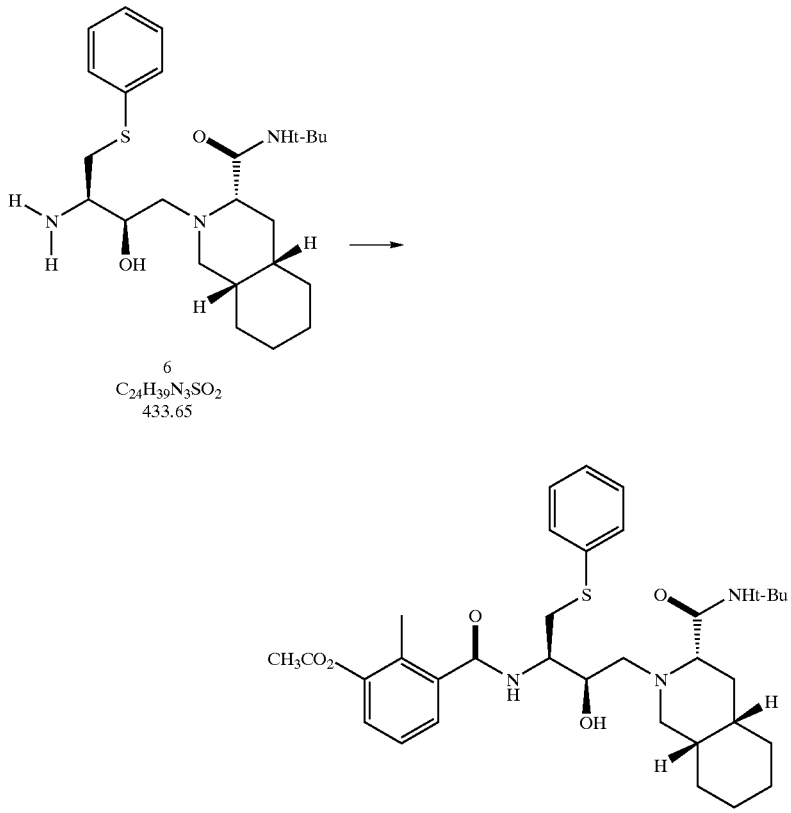

6
$C_{24}H_{39}N_3SO_2$
433.65

Acetate of Compound 4
$C_{36}H_{47}N_3O_3S$
609.83

| Chemicals | source | assay | Kg | L | d | mw | mol | equiv |
|---|---|---|---|---|---|---|---|---|
| Compound 6/EtOH | 1040-090 | | (0.746) | | | 433.65 | (1.72) | 1.00 |
| triethylamine | Fisher | | 0.26 | 0.36 | 0.726 | 101.19 | 2.58 | 1.50 |
| tetrahydrofuran | Fisher | | 0.40 | 0.45 | 0.889 | 72.11 | | |
| 3-acetoxy-2-methylbenzoyl chloride | AC1322 | 98.9% | 0.39 | | | 212.63 | 1.81 | 1.05 |
| Reference: | 1040-092 | | | | | | | |

The solution from Step A was cooled to 25° C., triethylamine (360 ml, 2.58 mol. 1.50 eq) was added to the solution, and the mixture was cooled to 7° C. (pH= 11.5–12.0). The mixture became hazy at 23° C. (Vol=9879 ml). This mixture was charged to a mixture of 3-acetoxy-2-methylbenzoyl chloride (388.5 g, 98.8 %, 1.81 mol, 1.05 eq) and tetrahydrofuran (440 ml) over 5 minutes. THF (10 ml) was used to complete the transfer. A 7.4° C. exotherm was observed. The mixture at the end of the addition was milky white. (Vol=10,717 ml). HPLC analysis after 30 minutes showed <0.2% of a compound of formula 6, 77% of the acetate of the compound of formula 4, 18.2% benzylalcohol, and no ester present. The milky mixture was used directly in the next step.

Step C: Saponification of Compound 4

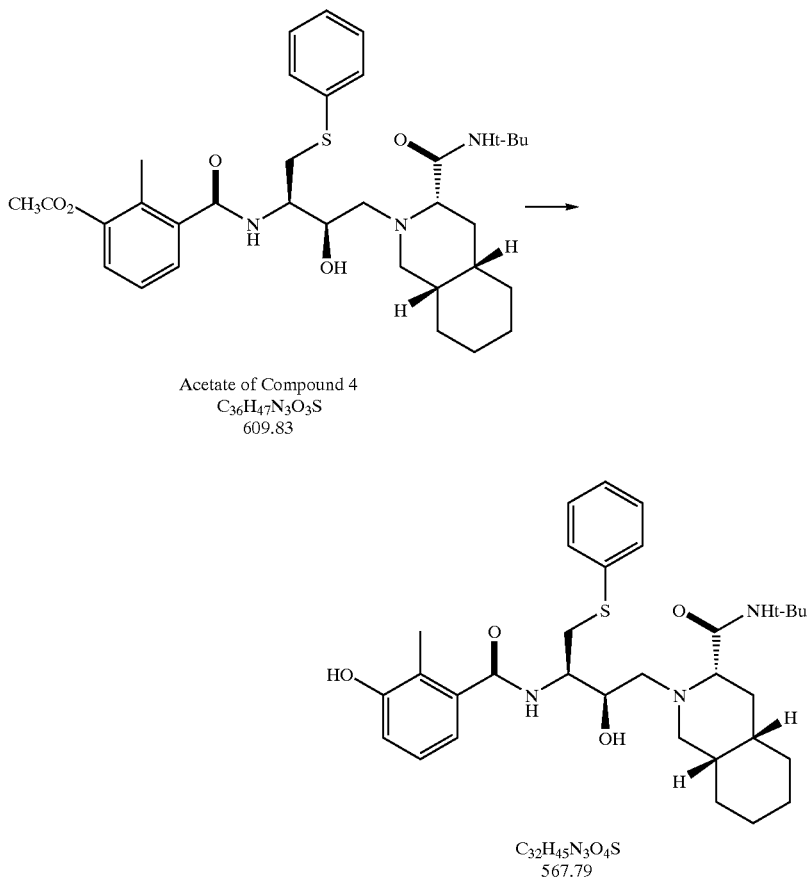

Acetate of Compound 4
$C_{36}H_{47}N_3O_3S$
609.83

$C_{32}H_{45}N_3O_4S$
567.79

| Chemicals | source | assay | Kg | L | d | mw | mol | equiv |
|---|---|---|---|---|---|---|---|---|
| Acetate of Compound 4/PA | 1040-092 | | (1.05) | | | 609.83 | (1.72) | 1.00 |
| NaOH | Fisher | 50% | 0.55 | 0.36 | 1.515 | 40.00 | 6.88 | 4.00 |
| Water | DI | | 15.0 | 15 | 1.000 | 18.02 | | |
| HOAc, glacial | Fisher | 17.4 N | 0.25 | 0.23 | 1.049 | 60.05 | 4.07 | 2.37 |
| Ethanol, (5% methanol) | McCormick | 95% | 0.04 | 0.05 | 0.785 | 46.07 | | |

NaOH (50%, 364 ml, 6.88 mol, 4.0 eq) was added to the mixture from Step B. The milky mixture became clear, then hazy, light brown. The mixture was agitated at 20° C. for 35 minutes. HPLC showed 15.9%. benzylalcohol, 78.6% of compound 4, and no acetate (Vol=11,081 ml). The mixture was heated to reflux and partially concentrated by atmospheric distillation until the head temperature reached 82° C. The distillate volume was 4275 ml The pH of the mixture was 14. The pot volume was measured (Vol=6000 ml).

Water (5 L) and HOAc (100 mL) were charged to a 12 L 3-neck round bottom flask fitted with a temperature probe and mechanical stirrer. The solution was heated to 54° C. (pH=2–2.5) (Vol=5100 ml). One half of the compound 4 mixture produced above (3 L) was added to this warm aqueous acetic acid solution to precipitate fine white solids. The pH was then adjusted to 7–7.5 with HOAc (19 ml), and the temperature was 53° C. (Vol=8119 ml). The solids were filtered off at 53° C. using isolated vacuum. The filtration was quick and easy. The reactor and wet cake were rinsed with warm (35° C.) water (2.5 L), and the filtrates were combined. The wet cake was pulled dry for 15–20 minutes.

Water (5 L) and HOAc (100 mL) were charged again to the 12 L 3-neck round bottom flask. The solution was heated to 41° C. (Vol=5100 ml). The remaining half of the compound 4 reaction mixture (3 L) was added to the new warm aqueous acetic acid solution to precipitate fine white solids. The pH was then adjusted to 7–7.5 with HOAc (15 ml). The temperature was 44° C. (Vol=8115 ml). The solids were filtered off at 53° C. using isolated vacuum. The filtration was quick and easy. The reactor and wet cake were rinsed with warm (35° C.) water (2.5 L), and the filtrates were combined. The wet cake was pulled dry for 15–20 minutes.

The two wet cakes (3587 g) were dried under vacuum at 60° C. for 90 hours to give a dry wt of 1075.38 g crude Compound 4. Theoretical yield is 977 g.

Step D: Purification of Compound 4

| Chemicals | source | assay | wt | ml | d | mw | mmol | equiv |
|---|---|---|---|---|---|---|---|---|
| Crude Compound 4 | 895-131 | 91.82% | 290 g | | | 567.79 | 469 | 1.00 |
| Acetone | Fisher | | 4038 g | 5105 | 0.791 | 58.08 | | |
| Water | DI | | 1070 g | 1070 | 1.000 | 18.02 | | |
| Celite | Aldrich | | 29 g | | | | | |
| Darco G-60 activated carbon | Fisher | | 44 g | | | 12.01 | | |

A 12 liter 3-neck RBF, fitted with a condenser, temperature probe, and mechanical stirrer, was charged with crude compound 4 (290 g, 92%, 469 mmol), activated carbon (Darco G-60, 44 g), acetone (4305 ml), and water (870 ml, DI). The mixture was heated to reflux (60–64° C.) and held 45 minutes (Vol=5509 ml). The hot slurry was filtered through celite (29 g) using isolated vacuum. The reactor and filter cake were rinsed with acetone (200 ml), and the clear, light yellow filtrates were combined. The mixture was allowed to cool slowly to 25° C. over 2.5 hours with stirring to precipitate a fine white solid (Vol=5665 ml). The white slurry was cooled to 0–10° C. and held for 1 hour. The solids were filtered off using isolated vacuum, and the liquid level was pulled through the surface of the wet cake. The reactor and wet cake were rinsed with a cold (0–10° C.) mixture of acetone/water (2:1, 300 ml). The liquid level was pulled through the surface of the wet cake, and the reactor and wet cake were again rinsed with a cold (0–10° C.) mixture of acetone/water (2:1, 300 ml). The wet cake was pulled as dry as possible using isolated vacuum and rubber damming to give a wet weight of 581 g. The product was dried under vacuum at 65° C. for 16 hours to give a dry weight of 221.61 g of compound 4. Theoretical yield was 266.28 g. HPLC and ROI analysis showed 99% and 0.14% respectively. Adjusted yield was 82%.

The present invention also is directed to novel methods of converting nelfinavir free base, compound 4, to nelfinavir mesylate, compound 7. These methods are described in more detail below, including the method for preparing compound 4 from compound 5 and the method for preparing compound 5.

Procedure for Preparation of Compound 5

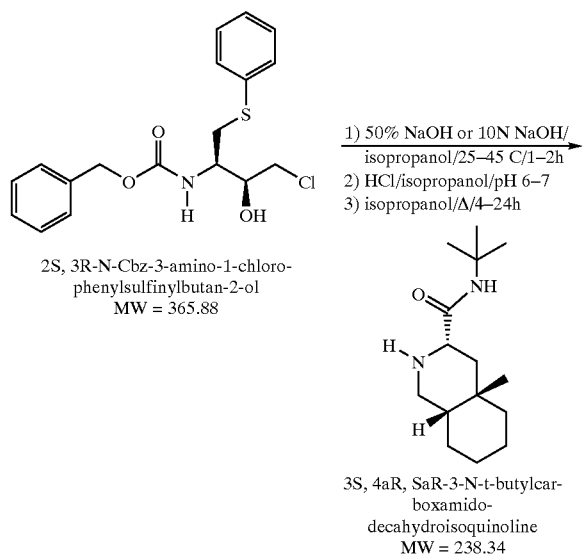

2S, 3R-N-Cbz-3-amino-1-chloro-phenylsulfinylbutan-2-ol
MW = 365.88

1) 50% NaOH or 10N NaOH/isopropanol/25–45 C/1–2h
2) HCl/isopropanol/pH 6–7
3) isopropanol/Δ/4–24h 3S, 4aR, 8aR-3-N-t-butylcarboxamido-decahydroisoquinoline
MW = 238.34

-continued

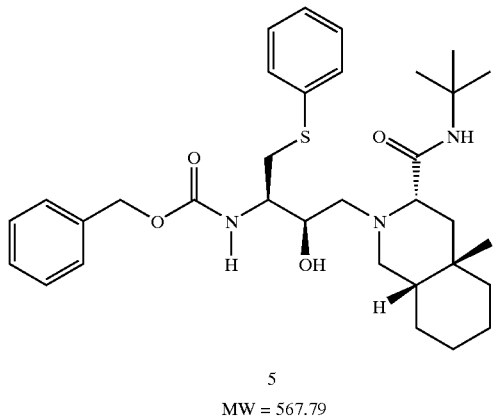

5
MW = 567.79

One equivalent 2S, 3R-N-Cbz-3-amino-1-chlorophenylsulfanylbutan-2-ol (which can be obtained from Kaneka Corporation or prepared as described in U.S. Pat. No. 5,484,926) is stirred in a sufficient volume of methanol, ethanol, isopropanol, or other low boiling alcoholic solvent at 20°–45° C. Isopropanol is the preferred solvent. A slight subcess of alkali base, such as sodium hydroxide or potassium hydroxide, as either an aqueous solution or as a solid, is added to this mixture with stirring. 10N sodium hydroxide is the preferred base. The mixture is stirred for 30 minutes to 24 hours until epoxide formation is complete. When the stir period is complete, the pH is adjusted to 6–7 with a proton acid such as HCl, either neat or dissolved in the reaction solvent.

A slight excess of 3S,4aR,8aR-3-N-t-butylcarboxamidodecahydroisoquinoline (which can be prepared as described in U.S. Pat. No. 5,256,783, which patent is entirely incorporated herein by reference) is added as either a dry solid or as a slurry to the reaction, and the mixture is heated to 40° C. to reflux for 12–24 hours or until the reaction is judged to be complete. Alternatively, 3S,4aR, 8aR-3-N-t-butylcarboxamidodecahydroisoquinoline can be introduced to the reaction at the same time that the 2S, 3R-N-Cbz-3-amino-1-chlorophenylsulfanylbutan-2-ol is charged to reactor. The epoxide formation is allowed to proceed as described. In this case, the reaction is not neutralized to a pH of 6–7, but a fixed amount of proton acid is added to neutralize excess base remaining. In either case, the reaction is partially concentrated in vacuo. The mixture is diluted with an equal volume of water and heated to reflux. Alternatively, the reaction is fully concentrated, and acetone or other ketonic solvent is added. The mixture can be filtered at this point, then an equal amount of water is added, and the mixture is heated. The resultant mixture is cooled with stirring. The resultant slurry is filtered, washed with aqueous solvent, and dried to yield compound 5.

Procedure for Preparation of Nelfinavir Free Base (Compound 4)

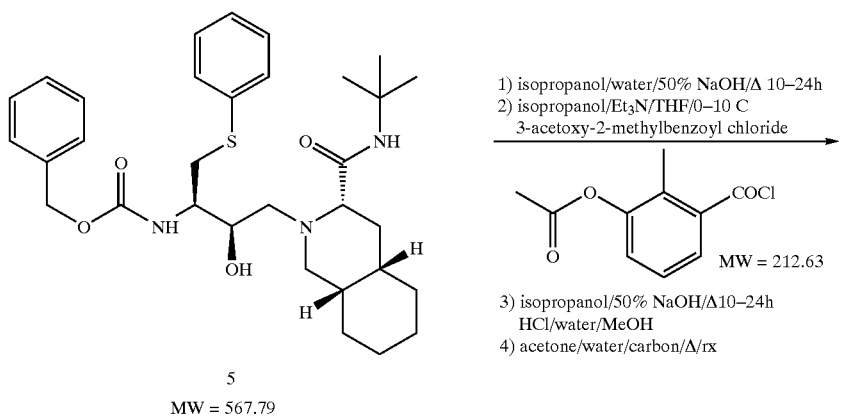

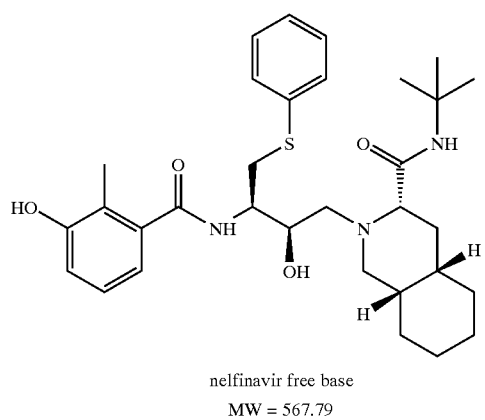

nelfinavir free base
MW = 567.79

In addition to the procedure described above, the following procedure can be used to convert compound 5 to the nelfinavir free base (compound 4):

One equivalent of compound 5, an excess of alkali base (such as sodium hydroxide or potassium hydroxide), and an alcoholic solvent (such as methanol, ethanol, or isopropanol) are combined, and the mixture is heated at reflux with stirring. 50% caustic soda is the preferred base and isopropanol is the preferred solvent. Water can be added to facilitate solubility of the base. When the reaction is judged complete, the mixture is cooled to 30° to 35° C., and the lower aqueous layer, if any, can be removed. The mixture is cooled to below 25° C. and an excess amount of organic base (such as diisopropylethyl amine or triethylamine) is added. Triethylamine is the base of choice.

A solution of excess 3-acetoxy-2-methylbenzbyl chloride in methanol, ethanol, isopropanol, THF, or other alcohol soluble solvents is slowly added to the cold mixture with stirring. THF is the preferred solvent.

An excess of alkali base, such as sodium hydroxide or potassium hydroxide, is added, and the mixture is heated at 40° C. to reflux with stirring. 50% caustic soda is the preferred base. When the reaction is judged complete, the mixture is cooled, and the lower aqueous layer is removed.

The reaction mixture is partially concentrated in vacuo. If deemed necessary, the mixture can be diluted with an alcohol solvent to facilitate stirring. Methanol is the preferred solvent. The mixture is added to aqueous acid to form a slurry. HCl is the preferred acid. The pH is adjusted to 7–8 with aqueous acid. The slurry is filtered and washed with water. The wet cake can be reslurried in water. The crude product is dried (partially or completely) or can be taken into the next step wet.

Either the dry or the crude, wet product is dissolved in aqueous acetone at reflux in the presence of activated carbon. The hot mixture is filtered, water is added, and the entire mixture is cooled with stirring to formn a slurry. The slurry is filtered, washed with aqueous acetone, and dried to give nelfinavir free base.

Other methods for preparing nelfinavir free base are disclosed in U.S. Pat. No. 5,484,926, and copending U.S. patent application of inventors S. Babu, B. Borer, T. Remarchuk, $R_1$ Szendroi, K. Whitten, J. Busse, and K. Albizati, entitled "Methods of Making HIV-Protease Inhibitors and Intermediates for Making HIV-Protease Inhibitors," U.S. patent application Ser. No. 08/708,607, filed on Sep. 5, 1996, which application is incorporated herein by reference.

Procedure for Spray Drying Nelfinavir Free Base to Obtain Nelfinavir Mesylate

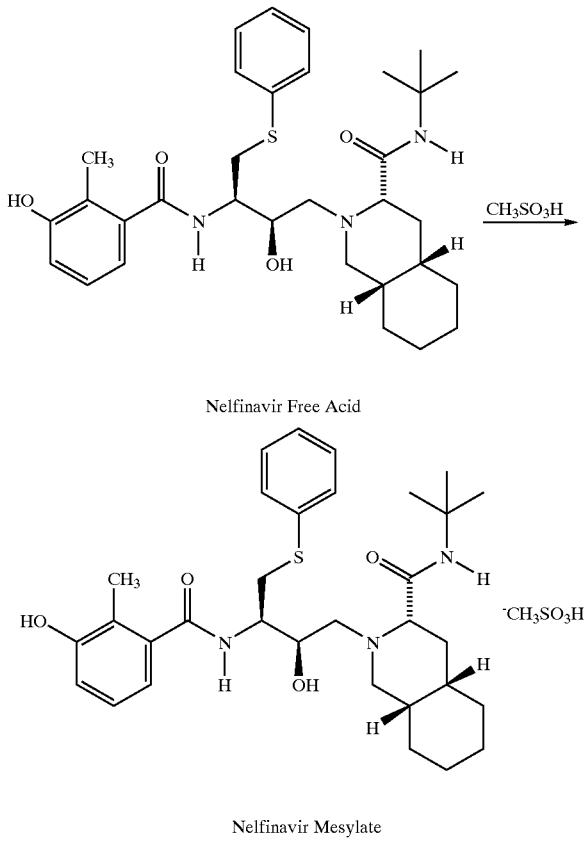

Nelfinavir Free Acid

⟶ CH₃SO₃H

Nelfinavir Mesylate

Generally, nelfinavir free base can be converted to nelfinavir mesylate using the following novel spray drying procedure.

Nelfinavir free base and an organic solvent (such as methanol, ethanol, isopropanol, THF, acetone, or MIBK) are mixed in a suitable vessel, and an equivalent amount of methanesulfonic acid is added. Ethanol is the preferred solvent. The mixture is stirred until nelfinavir mesylate is formed. The resultant slurry or solution is pumped into the spray dryer where the following settings are controlled:

| | |
|---|---|
| Inlet Temperature: | 100–190° C. |
| Outlet Temperature: | 60–120° C. |
| Atomizer Type: | vane, cocurrent flow, or counter current flow |
| Drying Gas Rate: | depends on equipment scale |

The inlet and outlet temperatures, feed rate, and atomizer type can be adjusted to optimize output and particle size distribution. Spray dried nelfinavir mesylate is collected at the spray dryer outlet collection point.

Specifically, this conversion was performed as described below.

19.4 kg±5% Alcohol (USP, 190 proof) and 6.00 kg±1% nelfinavir free base were added to a clean, dry 20–40L stainless steel container. The mixture was stirred until homogenous, then 1.04 kg±1% methanesulfonic acid, 99%, was added. The mixture was stirred until all solids were dissolved. A 0.2 µ filter cartridge was connected to the pump inlet, and the alcohol solution was pumped through the filter into the spray dryer set with the following initial settings:

| | |
|---|---|
| Inlet Temperature: | 160° C. |
| Outlet Temperature: | 90° C. |
| Wheel Type: | 50 mm vane wheel |
| Wheel Speed: | 27000 rpm |
| Drying Gas Rate: | 75 kgs./hour |

The inlet and outlet temperatures, feed rate, and wheel speed can be adjusted to optimize output and particle size distribution. The specific spray dryer used was a Niro Atomizer Portable Spray Dryer, type HT (equipped for inert gas) connected to an active carbon filter for removal of organic solvent residues. After the bulk of the solution had been spray dried, the mixing tank was rinsed into the spray dryer with 1.0 kg±5% Alcohol, USP, 190 proof. The spray dried nelfinavir mesylate was collected in 80–100% theory yield.

Procedure for Precipitaton of Nelfinavir Free Base to Obtain Nelfinavir Mesylate Alternatively, nelfinavir free base can be converted to nelfinavir mesylate using the following novel precipitation procedure.

Nelfinavir free base is slurried or dissolved in a suitable solvent (such as THF, methanol, or ethanol). THF is the preferred solvent. A molar equivalent amount of methanesulfonic acid is added, and the mixture is stirred until all solids dissolve. The solution is added to several volumes of an antisolvent (such as methyl t-butyl ether, diethyl ether, hexanes, or heptanes) that is rapidly stirring. Diethyl ether is the preferred antisolvent. After stirring, the mixture is filtered and washed with antisolvent. The solid is dried in a vacuum oven to yield nelfinavir mesylate.

Specifically, this conversion was performed as described below.

Nelfinavir free base (10.2 kg, 18.0 mol) and 24 L of tetrahydrofuran were added to a 100L reactor. Methanesulfonic acid (1.8 kg, 18.48 mol) also was added to the reactor. The reactor was stirred until all solids dissolved, and then the solution was filtered into a 100 gallon polypropylene tank containing 306 L methyl t-butyl ether or diethyl ether that was rapidly stirring. After stirring for 2 hours, the 100 gallon tank contents were filtered, washed with 17 L of methyl t-butyl ether or diethyl ether, and pulled as dry as possible. The solid was transferred to a rotocone drier and dried in a vacuum oven at 60–65° C. (at least 26 in. Hg or higher vacuum) for 12–72 hours or until the methyl t-butyl ether or diethyl ether content of the dried solid was below 1%. If necessary, the drier contents could be milled in a Fitzmill grinder to accelerate drying. Typical yields of nelfinavir mesylate range from 9 to 11 kg. (76%–92% theory).

In this application, Applicants have described certain theories and reaction mechanisms in an effort to explain how and why this invention works in the manner in which it works. These theories and mechanisms are set forth for informational purposes only. Applicants are not to be bound by any particular chemical, physical, or mechanical theory of operation.

While the invention has been described in terms of various preferred embodiments using specific examples, those skilled in the art will recognize that various changes and modifications can be made without departing from the spirit and scope of the invention, as defined in the appended claims.

We claim:
1. A method of making a compound of formula 4

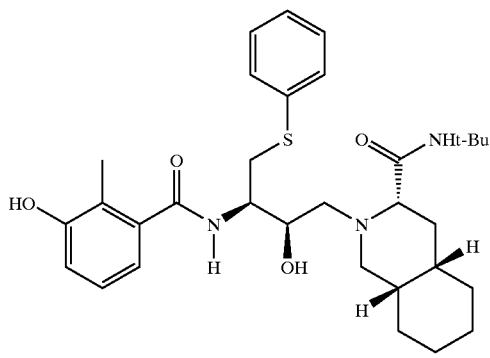

comprising: converting under sufficient conditions a compound of formula 3

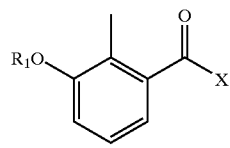

wherein $R_1$ is alkyl; cycloalkyl; heterocycloalkyl; aryl; heteroaryl; or a group of formula 8

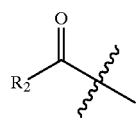

wherein $R_2$ is an alkyl group, a cycloalkyl group, a heterocycloalkyl group, or $O-R_6$, wherein $R_6$ is an alkyl group, an aralkyl group, or an aryl group;
or further wherein $R_1$ is a group of formula 9

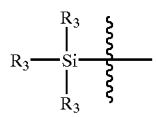

wherein each $R_3$ independently is an alkyl group, a cycloalkyl group, a heterocycloalkyl group, an aryl group, or a heteroaryl group;
or further wherein $R_1$ is a group of formula 10

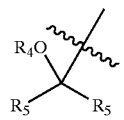

wherein $R_4$ and each $R_5$ independently are an alkyl group, a cycloalkyl group, a heterocycloalkyl group, an aryl group, or a heteroaryl group; and
X is OH; $OR_7$, wherein $R_7$ is alkyl or aryl; halogen; pseudohalogen; $OSO_2R_8$, wherein $R_8$ is alkyl or aryl; heteroaryl bonded through the heteroatom; or N-hydroxyheterocyclic bonded through the oxygen, to the compound of formula 4.
2. A method according to claim 1, wherein $R_1$ is —C(O)CH$_3$.

3. A method according to claim 1, wherein X is Cl.
4. A method according to claim 2, wherein $R_1$ is —C(O)CH$_3$.
5. A method of making a compound of formula 4

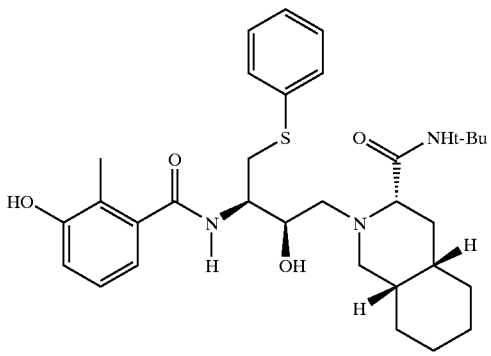

comprising:

deprotecting a compound of formula 5

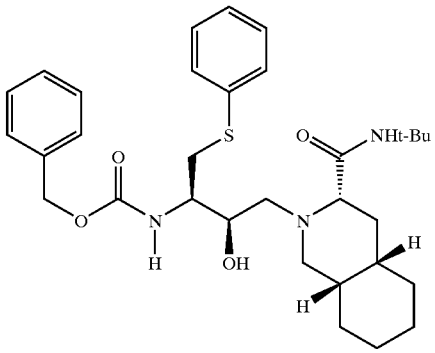

and adding to the deprotected compound of formula 5, under sufficient conditions, a compound of formula 3:

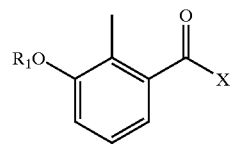

wherein $R_1$ is alkyl; cycloalkyl; heterocycloalkyl; aryl; heteroaryl; or a group of formula 8

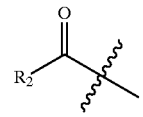

wherein $R_2$ is an alkyl group, a cycloalkyl group, a heterocycloalkyl group, or $O-R_6$, wherein $R_6$ is an alkyl group, an aralkyl group, or an aryl group;

or further wherein $R_1$ is a group of formula 9

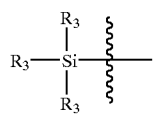

wherein each $R_3$ independently is an-alkyl group, a cycloalkyl group, a heterocycloalkyl group, an aryl group, or a heteroaryl group;

or further wherein $R_1$ is a group of formula 10

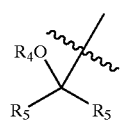

wherein $R_4$ and each $R_5$ independently are an alkyl group, a cycloalkyl group, a heterocycloalkyl group, an aryl group, or a heteroaryl group; and X is OH; $OR_7$, wherein $R_7$ is alkyl or alyl; halogen; pseudohalogen; $OSO_2R_8$, wherein $R_8$ is alkyl or aryl; heteroaryl bonded through the heteroatom; or N-hydroxyheterocyclic bonded through the oxygen, to form the compound of formula 4.

6. A method according to claim 5, wherein $R_1$ is —C(O)CH$_3$.

7. A method according to claim 5, wherein X is Cl.

8. A method according to claim 7, wherein $R_1$ is —C(O)CH$_3$.

9. A method of making a compound of formula 4

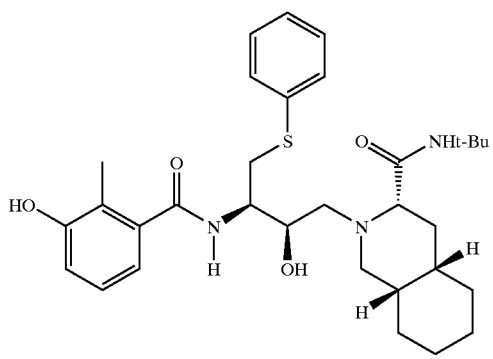

comprising: combining under sufficient conditions a compound of formula 3:

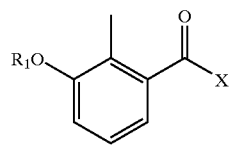

wherein $R_1$ is alkyl; cycloalkyl; heterocycloalkyl; aryl; heteroaryl; or a group of formula 8

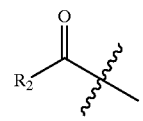

wherein $R_2$ is an alkyl group, a cycloalkyl group, a heterocycloalkyl group, or O—$R_6$, wherein $R_6$ is an alkyl group, an aralkyl group, or an aryl group;

or further wherein $R_1$ is a group of formula 9

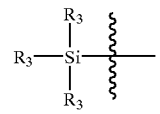

wherein each $R_3$ independently is an alkyl group, a cycloalkyl group, a heterocycloalkyl group, an aryl group, or a heteroaryl group;

or further wherein $R_1$ is a group of formula 10

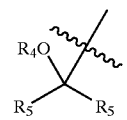

wherein $R_4$ and each $R_5$ independently are an alkyl group, a cycloalkyl group, a heterocycloalkyl group, an aryl group, or a heteroaryl group; and X is OH; $OR_7$, wherein $R_7$ is alkyl or aryl; halogen; pseudohalogen; $OSO_2R_6$, wherein $R_8$ is alkyl or aryl; heteroaryl bonded through the heteroatom; or N-hydroxyheterocyclic bonded through the oxygen, with a compound of formula 6

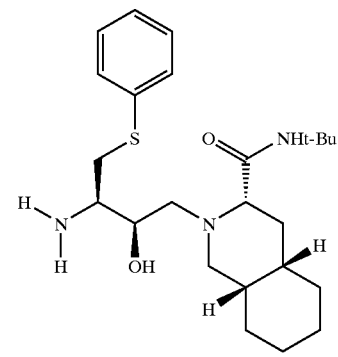

to obtain the compound of formula 4.

10. A method according to claim 9, wherein $R_1$ is —C(O)CH$_3$.

11. A method according to claim 9, wherein X is Cl.

12. A method according to claim 11, wherein $R_1$ is —C(O)CH$_3$.

13. A method of making a compound of formula 7

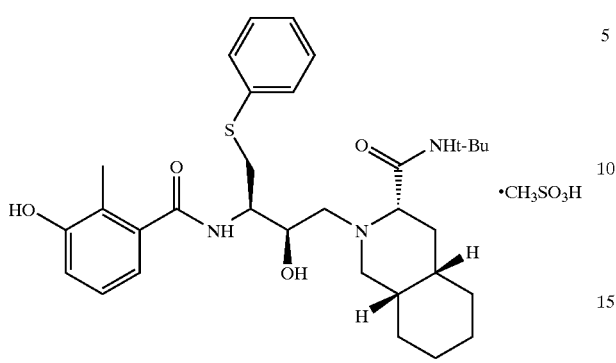

comprising: converting under sufficient conditions a compound of formula 4

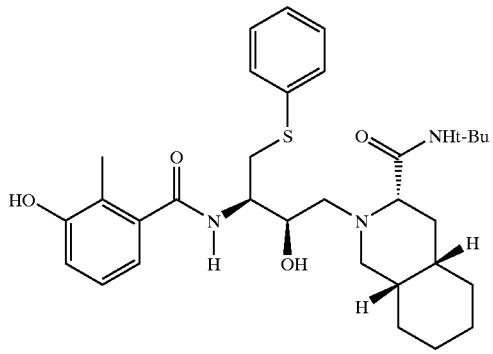

to the compound of formula 7 by:

(a) combining the compound of formula 4, a suitable solvent, and methanesulfonic acid to form the. compound of formula 7, the compound of formula 7 being dissolved in solution;

(b) adding a first antisolvent to the solution containing the compound of formula 7;

(c) agitating the compound of formula 7 and the first antisolvent to form a product having a solid phase and a liquid phase; and (d) filtering and washing the product with a second antisolvent, the second antisolvent being the same as or different from the first antisolvent, to obtain a solid.

14. A method according to claim 13, the method additionally comprising:

(e) drying the solid.

15. A method according to claim 13, wherein the suitable solvent is tetrahydrofuran.

16. A method according to claim 13, wherein the first antisolvent is diethyl ether.

17. A method of making a compound of formula 4

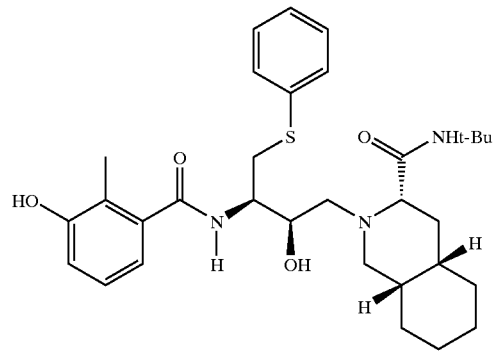

comprising: converting under sufficient conditions a compound of formula 2

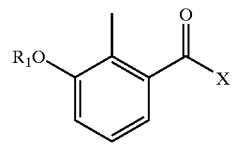

wherein $R_1$ is alkyl; cycloalkyl; heterocycloalkyl; aryl; heteroaryl; a group of formula 8

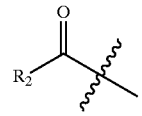

wherein $R_2$ is an alkyl group, a cycloalkyl group, a heterocycloalkyl group, or $O-R_6$, wherein $R_6$ is an alkyl group, an aralkyl group, or an aryl group;

or further wherein $R_1$ is a group of formula 9

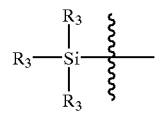

wherein each $R_3$ independently is an alkyl group, a cycloalkyl group, a heterocycloalkyl group, an aryl group, or a heteroaryl group;

or further wherein $R_1$ is a group of formula 10

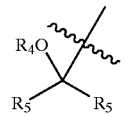

wherein $R_4$ and each $R_5$ independently are an alkyl group, a cycloalkyl group, a heterocycloalkyl group, an aryl group, or a heteroaryl group; to the compound of formula 4.

18. A method according to claim 17, wherein $R_1$ is $-C(O)CH_3$.

19. A method of making a compound of formula 7

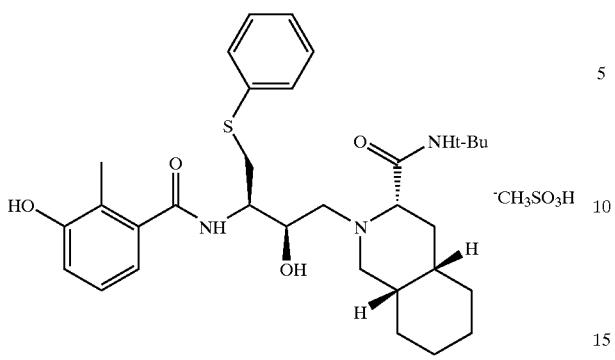

comprising:

deprotecting a compound of formula 5

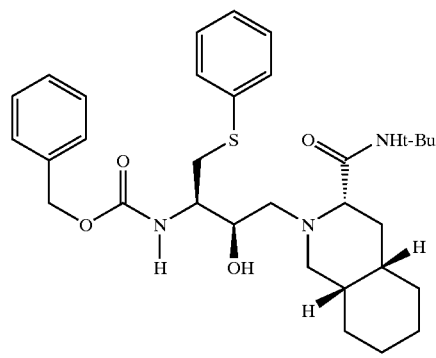

adding to the deprotected compound of formula 5, under sufficient conditions, a compound of formula 3:

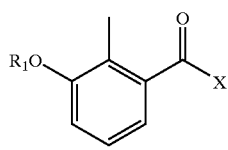

wherein $R_1$ is alkyl; cycloalkyl; heterocycloalkyl; aryl; heteroaryl; or a group of formula 8

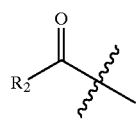

wherein $R_2$ is an alkyl group, a cycloalkyl group, a heterocycloalkyl group, or O—$R_6$, wherein $R_6$ is an alkyl group, an aralkyl group, or an aryl group;

or further wherein $R_1$ is a group of formula 9

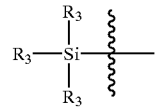

wherein each $R_3$ independently is an alkyl group, a cycloalkyl group, a heterocycloalkyl group, an aryl group, or a heteroaryl group;

or further wherein $R_1$ is a group of formula 10

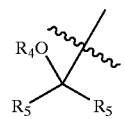

wherein $R_4$ and each $R_5$ independently are an alkyl group, a cycloalkyl group, a heterocycloalkyl group, an aryl group, or a heteroaryl group; and X is OH; $OR_7$, wherein $R_7$ is alkyl or aryl; halogen; pseudohalogen; $OSO_2R_8$, wherein $R_8$ is alkyl or aryl; heteroaryl bonded through the heteroatom; or N-hydroxyheterocyclic bonded through the oxygen, to form a compound of formula 4:

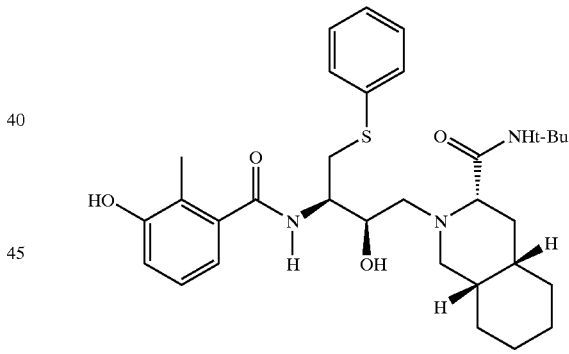

and converting the compound of formula 4 to the compound of formula 7.

* * * * *

UNITED STATES PATENT AND TRADEMARK OFFICE
CERTIFICATE OF CORRECTION

PATENT NO. : 6,605,721 B2
DATED : August 12, 2003
INVENTOR(S) : Michael E. Deason et al.

It is certified that error appears in the above-identified patent and that said Letters Patent is hereby corrected as shown below:

Title page,
Item [56], References Cited, OTHER PUBLICATIONS,
"Celis et al., ... etc." reference, "coli"" should read -- Coli" --;
"Menge et al., ... etc." reference, "role" should read -- Role --;
"Mukharji et al., ... etc." reference, "Chem.EN." should read -- Chem. EN." --;
"Ozturk et al., ... etc." reference, "cyclic" should read -- Cyclic --; and
"Townsend et al., ... etc." reference, "chiral" should read -- Chiral --.

Column 1,
Line 31, "Feb. 2, 1994" should read -- Feb. 2, 1994, now U.S. Patent No. 5,484,926 --; and
Line 32, "Jun. 7, 1995" should read -- Jun. 7, 1995, now U.S. Patent No. 5,846,993 --.

Column 10,
Line 61, "dred" should read -- dried --.

Column 15,
Line 40, "7." should read -- 7, --.

Column 18,
Line 3, "atom's" should read -- atoms --.

Column 19,
Line 20, "butare" should read -- but are --.

Column 21,
Line 24, "polarorganic" should read -- polar organic --; and
Line 25, "dimethyiformamide," should read -- dimethylformamide --.

Column 22,
Line 40, "like." should read -- like --; and
Line 50, "boron- based" should read -- boron-based --.

Column 26,
Line 49, "extractor,, and" should read -- extractor, and --.

UNITED STATES PATENT AND TRADEMARK OFFICE
CERTIFICATE OF CORRECTION

PATENT NO. : 6,605,721 B2
DATED : August 12, 2003
INVENTOR(S) : Michael E. Deason et al.

It is certified that error appears in the above-identified patent and that said Letters Patent is hereby corrected as shown below:

Column 27,

Line 11, "
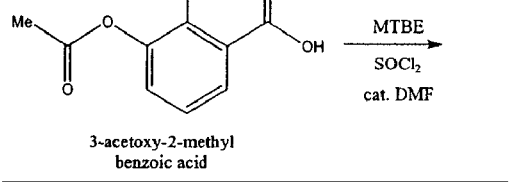
"

should read --
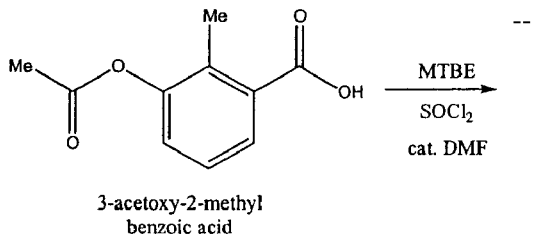
--

Column 28
Line 11, "Bochi" should read -- Biichi --; and
Line 34, "3-Acetoxy52-methylbenzoyl" should read -- 3-Acetoxy-2-methylbenzoyl --.

Column 31
Line 41, "$C_{36}H_{47}N_3O_3S$" should read -- $C_{36}H_{47}N_3O_5S$ --.

Column 33,
Line 4, "$C_{36}H_{47}N_3O_3S$" should read -- $C_{36}H_{47}N_3O_5S$ --;
Line 51, "15.9%." should read -- 15.9% --; and
Line 55, "4275 ml" should read -- 4275 ml. --.

Column 35,
Line 14, "fifted" should read -- fitted --; and
Line 63, "3S, 4aR, SaR-3-N-t-butylcar-" should read -- 3S, 4aR, 8aR-3-N-t-butylcar- --.

Column 37,
Line 56, "3-acetoxy-2-methylbenzbyl" should read -- 3-acetoxy-2-methylbenzoyl --.

Column 38,
Line 54, "formn" should read -- form --; and
Line 62, "$R_1$" should read -- R. --.

UNITED STATES PATENT AND TRADEMARK OFFICE
CERTIFICATE OF CORRECTION

PATENT NO. : 6,605,721 B2
DATED : August 12, 2003
INVENTOR(S) : Michael E. Deason et al.

It is certified that error appears in the above-identified patent and that said Letters Patent is hereby corrected as shown below:

Column 42,
Line 2, "claim 2," should read -- claim 3, --.

Column 43,
Line 9, "an-alkyl" should read -- an alkyl --.

Column 44,
Line 38, "$OSO_2R_6$," should read -- $OSO_2R_8$, --.

Signed and Sealed this

Twenty-seventh Day of April, 2004

JON W. DUDAS
*Acting Director of the United States Patent and Trademark Office*